(12) United States Patent  
Prescott

(10) Patent No.: US 7,665,279 B2
(45) Date of Patent: Feb. 23, 2010

(54) SUTURE WINDING DEVICE AND METHODS OF USE THEREOF

(75) Inventor: Michael Prescott, Hamden, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 88 days.

(21) Appl. No.: 12/002,254

(22) Filed: Dec. 14, 2007

(65) Prior Publication Data

US 2008/0093231 A1    Apr. 24, 2008

Related U.S. Application Data

(63) Continuation of application No. 11/809,081, filed on May 31, 2007, which is a continuation-in-part of application No. 11/373,366, filed on Mar. 10, 2006, now Pat. No. 7,322,161.

(60) Provisional application No. 60/661,184, filed on Mar. 11, 2005.

(51) Int. Cl.
*B65B 63/04* (2006.01)
(52) U.S. Cl. .................. 53/430; 53/116; 206/63.3
(58) Field of Classification Search .............. 53/430, 53/116; 206/63.3; 242/129, 362
See application file for complete search history.

(56) References Cited

U.S. PATENT DOCUMENTS

| 5,123,528 A | 6/1992 | Brown et al. |
| 5,179,818 A | 1/1993 | Kalinski et al. |
| 5,368,599 A | 11/1994 | Hirsch et al. |
| 5,473,854 A | 12/1995 | Demarest et al. |
| 5,491,954 A | 2/1996 | Sobel |
| 5,500,991 A | 3/1996 | Demarest et al. |
| 5,533,611 A | 7/1996 | Bordighon et al. |
| 5,667,155 A | 9/1997 | Cerwin et al. |
| 5,695,138 A | 12/1997 | Daniele et al. |
| 5,788,062 A | 8/1998 | Cerwin et al. |
| 6,138,440 A | 10/2000 | Gemma |
| 6,283,297 B1 | 9/2001 | Mosley |
| 6,463,719 B2 | 10/2002 | Dey et al. |
| 7,322,161 B2 * | 1/2008 | Prescott ................ 53/116 |
| 2005/0035007 A1 | 2/2005 | Kennedy et al. |
| 2006/0201828 A1 * | 9/2006 | Prescott ................ 206/63.3 |

FOREIGN PATENT DOCUMENTS

| EP | 0 667 123 | 8/1996 |
| EP | 0 755 657 | 1/1997 |
| EP | 0 884 023 | 12/1998 |
| EP | 1700570 | 9/2006 |

OTHER PUBLICATIONS

European Search Report for EP 08251863.0-2310 date of completion is Feb. 13, 2009 (8 pages).

\* cited by examiner

*Primary Examiner*—Stephen F Gerrity

(57) ABSTRACT

A suture winding device is provided that includes a holder and a base having a needle holder for receiving a needle with a quantity of attached suture attached thereto. A plurality of rods is disposed on the base that may be arranged in one or more arrays. The plurality of rods at contribute to the alignment of a retainer disposed on the base that includes first and second members that may be joined together using pressure and/or heat. Prior to joining the first and second members of the retainer, the base may be rotated to form loops of suture around the arrays of rods.

14 Claims, 20 Drawing Sheets

SUTURE WINDING DEVICE AND METHODS OF USE THEREOF

CROSS-REFERENCE TO RELATED APPLICATIONS

This application is a continuation of U.S. patent application Ser. No. 11/809,081, filed on May 31, 2007, which is a continuation-in-part of U.S. patent application Ser. No. 11/373,366, filed Mar. 10, 2006, now U.S. Pat. No. 7,322,161, which claims priority to U.S. Provisional Patent Application Ser. No. 60/661,184, filed Mar. 11, 2005. The entire contents of each of these prior applications are incorporated by reference herein.

BACKGROUND

1. Technical Field

The present disclosure relates to devices and methods for packaging sutures and, more particularly, to a suture winding device and methods for use thereof.

2. Background of Related Art

Packages for surgical sutures having needles attached at one or both ends are typically constructed according to the nature of the suture material and to how the sutures will be used. Generally, the package holds the suture and attached needles in place, protects them during handling and storage, and allows ready access to the suture for removal with minimum handling at the time the suture is to be used.

The packages are loaded with one or more needles that have a desired quantity of suture attached. After positioning the needle or needles in the package, the attached suture is generally looped within the package using tracks, rods, posts, or other suitable positioning structures located within the package.

An example of one such package is disclosed in U.S. Pat. No. 5,123,528 to Brown et al., currently owned and assigned to United States Surgical, that discloses a package having a number of tracks and a needle receiving park. Each track has a suture receiving port and an opposed vacuum port. By applying vacuum to the vacuum receiving ports, a quantity of suture is drawn through the suture receiving port and received in the track. After a predetermined quantity of suture is received by the track, a needle attached to the suture is positioned in the needle receiving park.

A device for winding a quantity of suture attached to a needle is disclosed in U.S. Pat. No. 5,473,854 to Demarest et al. that discloses an apparatus having a number of workstations for packaging needles with an attached suture. As a turntable of the apparatus rotates, a tool nest attached to the turntable is rotated from one workstation to the next workstation. Each workstation performs a specific task with respect to packaging the needle with attached suture.

SUMMARY

The present disclosure is directed to an apparatus for use with a suture package or retainer and one or more sutures. According to one embodiment, the apparatus includes a base member, which may be rotatably mounted to a plate, a needle holder disposed within the base member, at least one needle that is adapted for releasable engagement with the needle holder and attached to a quantity of suture, a retainer package disposed atop the base member and including a first member having a plurality of throughholes, a plurality of rods configured in at least one array that are engagable with, and correspond to, the throughholes, and a holder having open and closed states. The holder is movable relative to the base member between a first position and at least one subsequent position, either manually or automatically, and includes a first arm and a second arm. In the open state, the first and second arms are in spaced apart relation and in the closed state, at least a portion of the first arm is in substantial contact with at least a portion of the second arm.

The holder may slidably engage at least a portion of the suture in the closed state such that a predetermined amount of tension may be applied thereto.

The first member of the retainer may be adapted to receive the needle in the needle holder and may additionally include a slot for receiving a portion of the suture.

In one aspect of the present disclosure, the rods of the at least one array are movable from a retracted position to an extended position in which the rods are releasably engagable with the suture.

In another aspect of the present disclosure, rotation of the base member corresponds to movement of the rods into the extended position such that at least a portion of the suture is wound about the rods thereby forming a plurality of loops.

In yet another aspect of the present disclosure, the at least one array includes a first array and at least one additional array. The rods of the first array and the at least one additional array are independently and sequentially movable from the retracted position to the extended position and are arranged in a first arc and at least one additional arc. It is contemplated that the first arc may define a smaller radius than the at least one additional arc such that each of the plurality of loops are in space apart relation and each define a diameter that is larger than that of the previous loop.

In another embodiment, an apparatus for packaging a suture is disclosed that includes a base member having a first holder disposed therein, at least one array disposed substantially along a longitudinal axis of the base member and including at least one rod, a retainer package that has at least a first member with at least one throughhole configured to releasably receive the at least one rod of the at least one array, a second holder that includes first and second arms, and a parking mechanism having open and closed conditions. The second holder is movably connected to the base member and is movable between a first position and at least one subsequent position.

In the open condition, the first and second arms of the parking mechanism are in spaced apart relation, and in the closed condition, at least a portion of the first arm is in substantial contact with at least a portion of the second arm. The parking mechanism may be movable relative to the base member between a first position and at least one subsequent position. The present disclosure contemplates that the parking mechanism may be in the closed condition when the parking mechanism is in the at least one subsequent position, and that in the closed condition, the parking mechanism releasably retains at least a portion of the suture.

In yet another embodiment, the apparatus may also include at least one positioning rod that is movable from a retracted position to an extended position in which the at least one positioning rod is engagable with at least a portion of the suture. In still another embodiment, the at least one positioning rod is in the extended position when the parking mechanism is in the at least one subsequent position such that at least a portion of the suture is disposed within the parking device and about the positioning rod.

At least a portion of the suture may form an angle with respect to an axis of the base member that is in the range of approximately 0° to approximately 180°.

BRIEF DESCRIPTION OF THE DRAWINGS

Embodiments of the presently disclosed suture winding device are described herein with reference to the drawings, wherein.

DETAILED DESCRIPTION OF THE EMBODIMENTS

Figure 1:
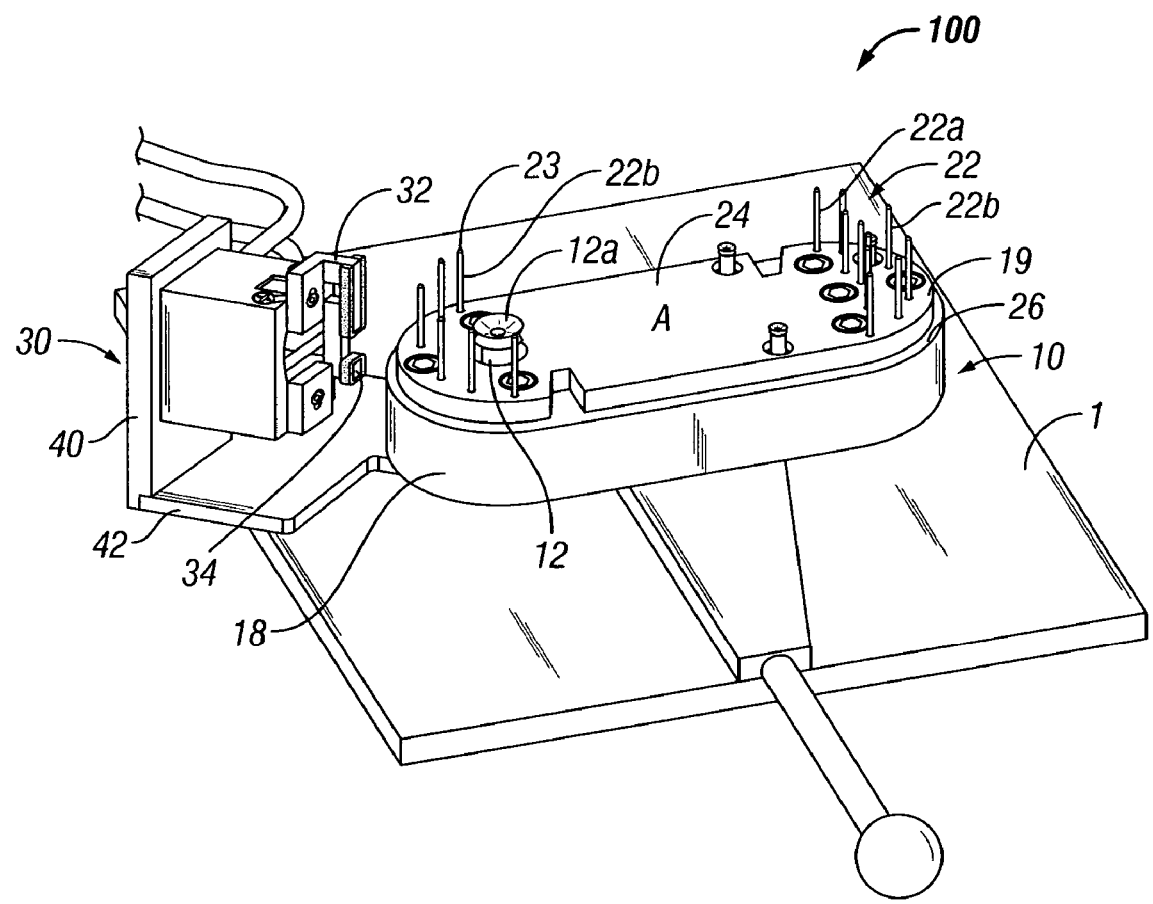
FIG. 1 is a perspective view of one embodiment of the presently disclosed suture winding device with an embodiment of a holder.

Embodiments of the presently disclosed suture winding device will now be described in detail with reference to the drawings, in which like reference numerals designate identical or corresponding elements in each of the several views.

Referring initially to FIG. 1, the suture winding device, shown generally as 100, includes a base 10 that is rotatably attached to a support plate 1 and is rotatable about a central point A.

Figure 2:
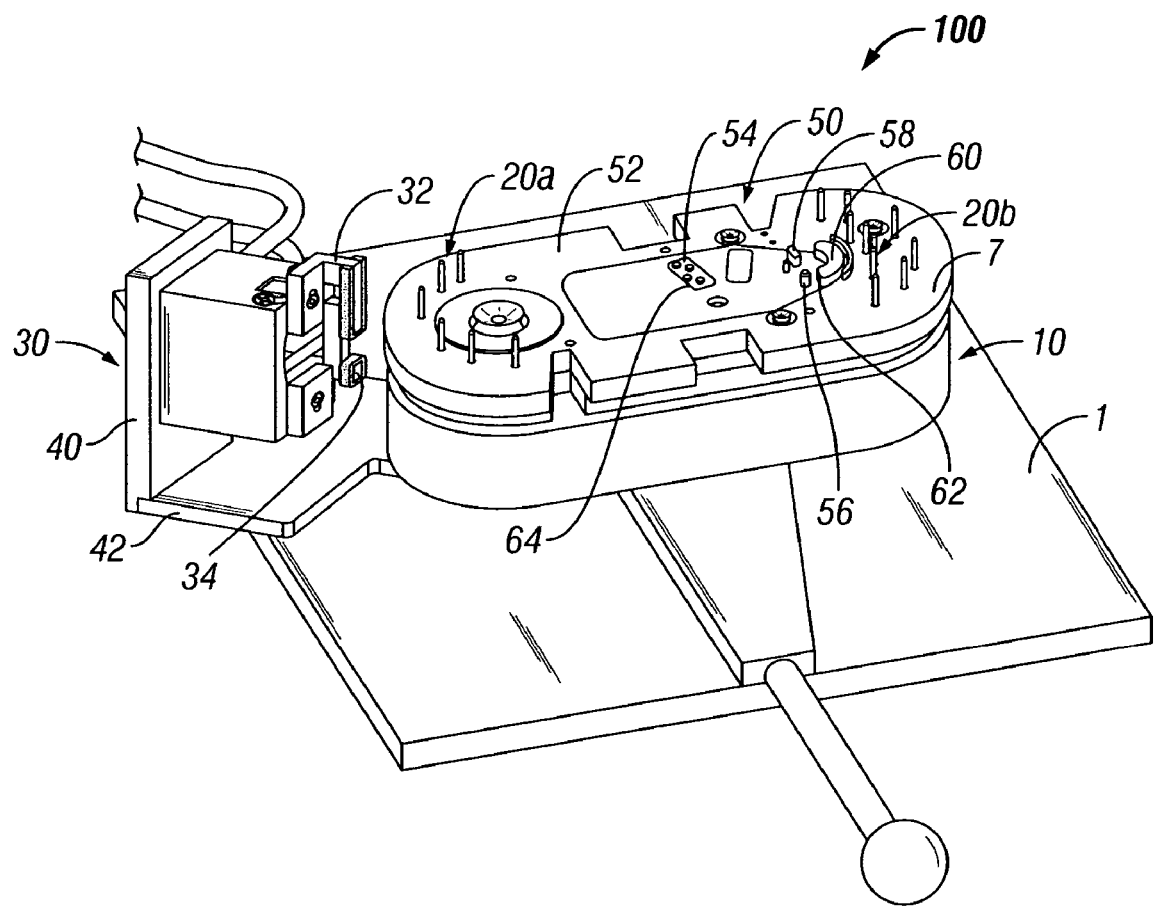
FIG. 2 is a perspective view of the suture winding device of FIG. 1 including a mounting member.

As shown in FIGS. 1 and 2, base 10 includes a frame 18 and a plate 19 that is attached to a mounting surface 26 of frame 18. In an embodiment of suture winding device 100, frame 18, and plate 19 have a generally oval or elongate elliptical configuration. Other shapes may also be used and are contemplated herein. Base 10 further includes a plurality of vacuum connections 12 where each vacuum connection includes a vacuum port 12a. Each vacuum connection 12 is fluidly coupled to a vacuum source (not shown) such as would be known by a person of ordinary skill in the art. The actuation of vacuum connections 12 (i.e. applying negative pressure or suction to vacuum ports 12a) may be controlled manually or automatically.

In addition to vacuum connections 12, a plurality of rods 22 is arranged on plate 19 and at least a portion of each rod 22 extends through top surface 24. Each rod 22 includes a tip 23 that is configured and dimensioned to extend beyond a top surface of a mounting member 7 (FIG. 2). In one embodiment, rods 22 include interior rods 22a and exterior rods 22b. In suture winding device 100, the plurality of rods 22 may be arranged to form a first array 20a and a second array 20b. In one embodiment of suture winding device 100, first array 20a and second array 20b are generally arcuate arrangements of exterior rods 22b that are spaced apart along a longitudinal axis of base 10.

Figure 5:
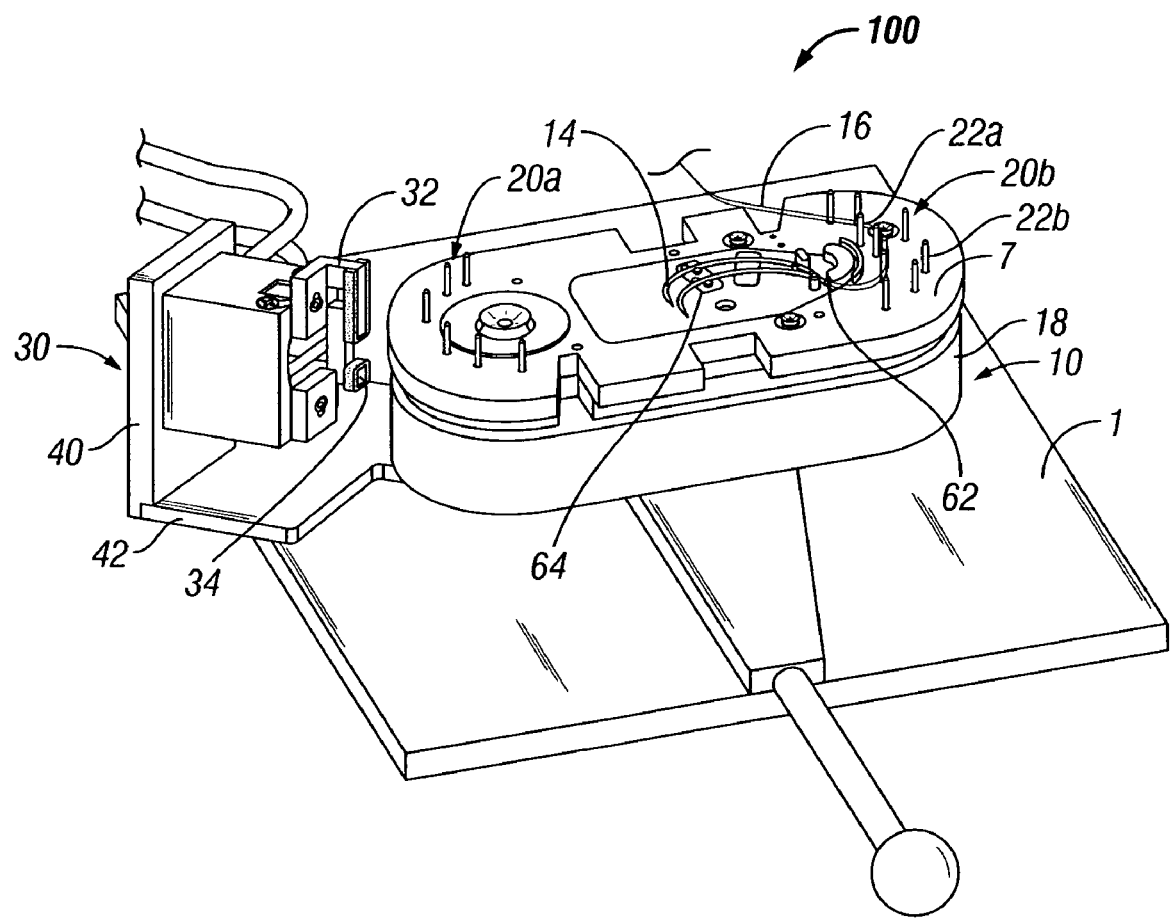
FIG. 5 is a perspective view of the suture winding device of FIG. 1 with a pair of needles having a length of suture disposed in a needle holder and the holder being in a loading position.

A needle holder 50 is disposed in a central region of mounting member 7 (FIG. 2) and separates first array 20a from second array 20b. Mounting member 7 is disposed on base 10 such that it abuts top surface 24. Needle holder 50 is releasably disposed in mounting member 7 and includes a plate 52 having a plurality of buttons 54 disposed thereon. In an embodiment of suture winding device 100, buttons 54 are arranged in pairs to form one or more needle channels 64. Each needle channel 64 is configured and adapted for releasably engaging a needle 14 (FIG. 5). Needle 14, as is known in the art, has a sharpened tip at one end and a length of suture 16 extending from an opposing end. Disposed on one end of plate 52 are a post 56, a needle guide 58, and an end member 60. Post 56 and end member 60 are spaced apart to form a suture channel 62 therebetween. Needle guide 58 in cooperation with buttons 54 position needle 14 in needle holder 50 such that suture 16 is releasably received in suture channel 62 (FIG. 5). In one embodiment, suture 16 is positioned on mounting member 7 such that it contacts at least one interior rod 22a (FIG. 5). Needle holder 50 may be replaced by alternate embodiments of the needle holder that are configured to receive single needles, double needles, or needles of varying diameters and dimensions regardless of whether the needles are in a single or double configuration.

Figure 17:
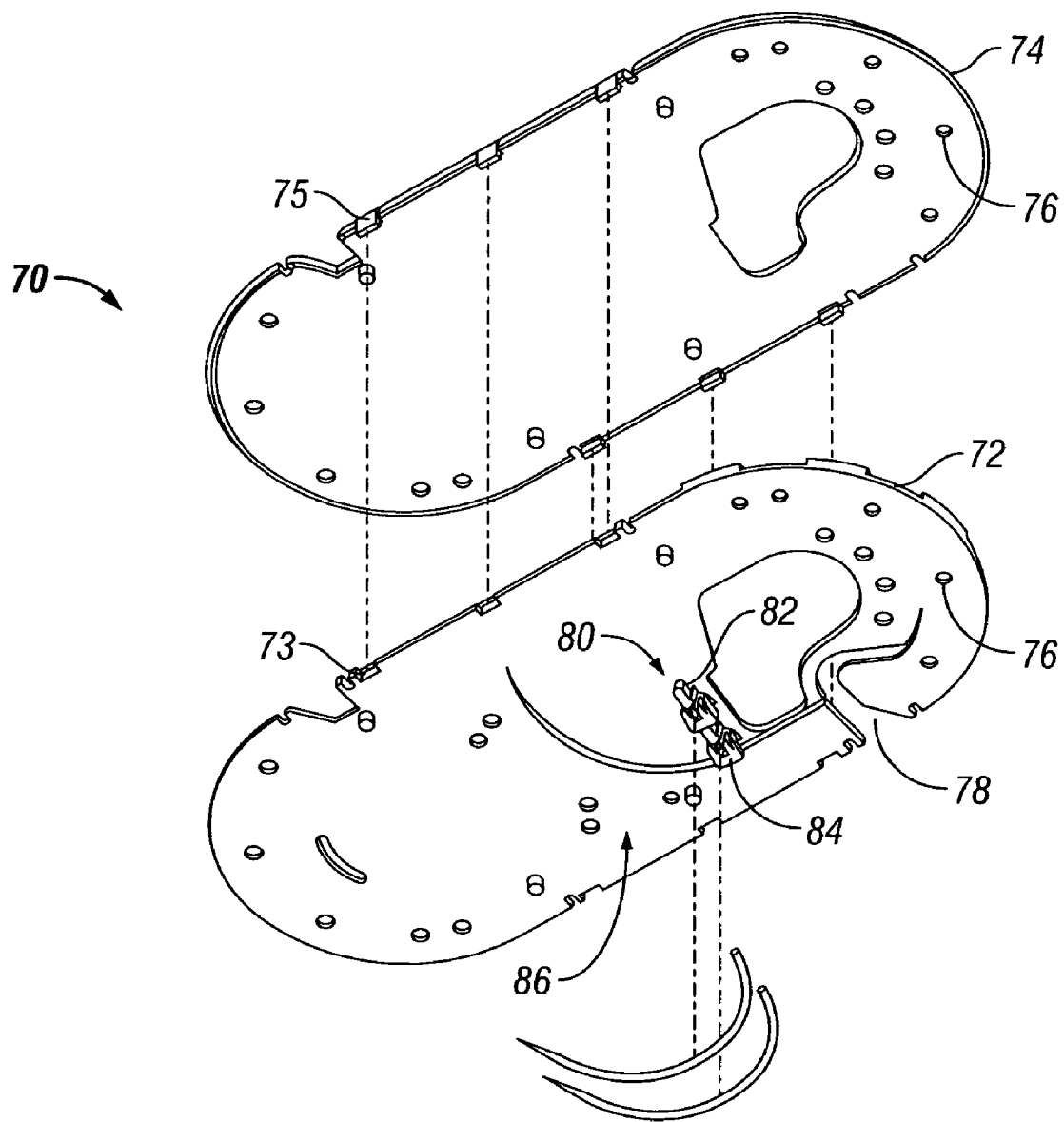
FIG. 17 is an exploded perspective view of an embodiment of the retainer.

A suture package or retainer 70 (FIG. 17) is positionable on base 10 as illustrated in FIGS. 6-8 and 15. A suitable retainer 70 is the subject matter of U.S. patent application Ser. No. 10/891,604 filed on Jul. 15, 2004, currently owned and assigned to Tyco Healthcare Group, the contents of which are hereby incorporated by reference in their entirety. Referring now to FIG. 17, retainer 70 includes a first member 72 and a second member 74. Second member 74 is adapted to attach to first member 72 as will be discussed in further detail below.

Figure 6:
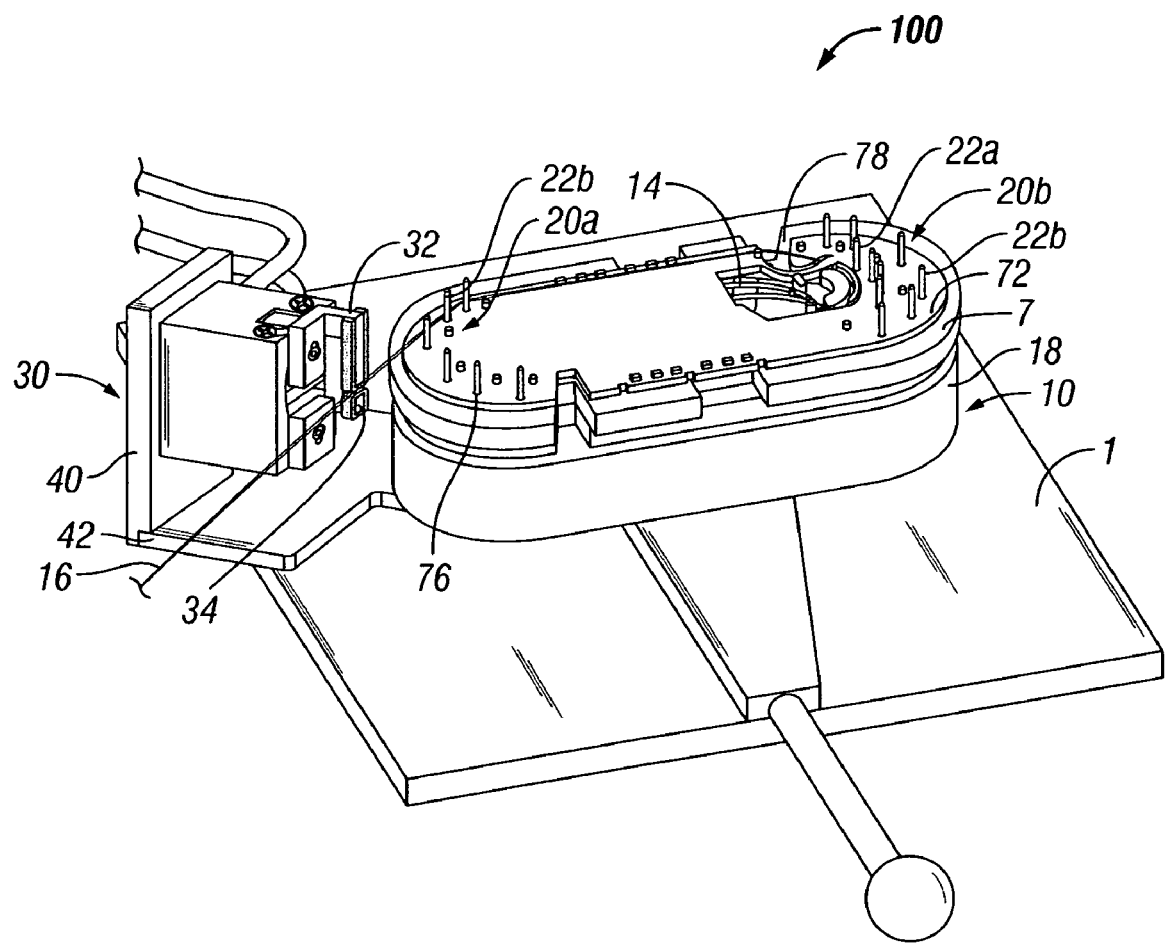
FIG. 6 is a perspective view of the suture winding device of FIG. 5 with a first member of a retainer positioned thereon.

With reference to FIG. 6, first member 72 is shown disposed on mounting member 7 of base 10. In one embodiment, the position of first member 72 with respect to mounting member 7 is maintained by vacuum connections 12 (FIG. 1) that are disposed in base 10. More specifically, vacuum applied through vacuum connections 12 holds first member 72 to vacuum ports 12a. First member 72 is disposed on top of mounting member 7. Positioned between first member 72 and mounting member 7 is needle 14 with a length of suture 16 attached thereto. First member 72 includes a plurality of throughholes 76 arranged to correspond with rods 22 (FIG. 1) of base 10 thereby aligning needle holder 50 with a needle park or needle grip 80 of first member 72. As shown in FIG. 17, first member 72 includes needle park 80 for releasably attaching needle 14 to first member 72. Needle park 80 is positioned on first member 72 such that is aligned with needle holder 50 when first member 72 is positioned on plate 19 by the cooperative arrangement of rods 22 and throughholes 76. As with needle holder 50, needle park 80 may be replaced by alternate embodiments that are configured to receive single needles, double needles, or needles of varying diameters and dimensions regardless of whether the needles are in a single or double configuration.

Needle park 80 includes a number of tabs 82 and notches 84 that extend from a surface of first member 72 towards plate 19. In one embodiment, needle holder 80 is disposed in a recess 86 on an underside of first member 72. Each tab 82 and its corresponding notch 84 are configured and adapted for releasably gripping needle 14 such that when retainer 70 is removed from base 10, needle 14 separates from needle holder 50 and is releasably attached to retainer 70 by needle park 80. Tabs 82 and notches 84 are biased towards each other for releasably receiving needle 14. A slot 78 is disposed along an edge of first member 72 where slot 78 communicates with recess 86 such that a portion of suture 16 may extend through recess 86 and be accessed from outside retainer 70.

Transfer of needle 14 from needle holder 50 to needle park 80 is affected by forces applied by an operator in a generally downward direction (i.e. towards plate 19) on first member 72. As first member 72 is urged towards plate 19 and needle holder 50, needle 14 contacts needle park 80 with sufficient force to overcome the bias of tab 82 and notches 84. By overcoming the bias of tabs 82 and notches 84, the space between tab 82 and notches 84 is sufficient to receive needle 14. After first member 72 has moved a predetermined distance, needle 14 no longer urges tab 82 and notches 84 away from each other whereupon the bias of tab 82 and notches 84 act to urge them towards each other for releasably retaining needle 14. In configurations including more than one needle 14, each set of tab 82 and notches 84 is configured as previously described. Alternatively, vacuum applied to first member 72 through vacuum ports 12a may supply the forces that urge needle 14 into releasable engagement with needle park 80 as previously discussed. In another embodiment, a combination of applied vacuum and operator action supply the forces for urging needle 14 into releasable engagement with needle park 80.

Figure 7:
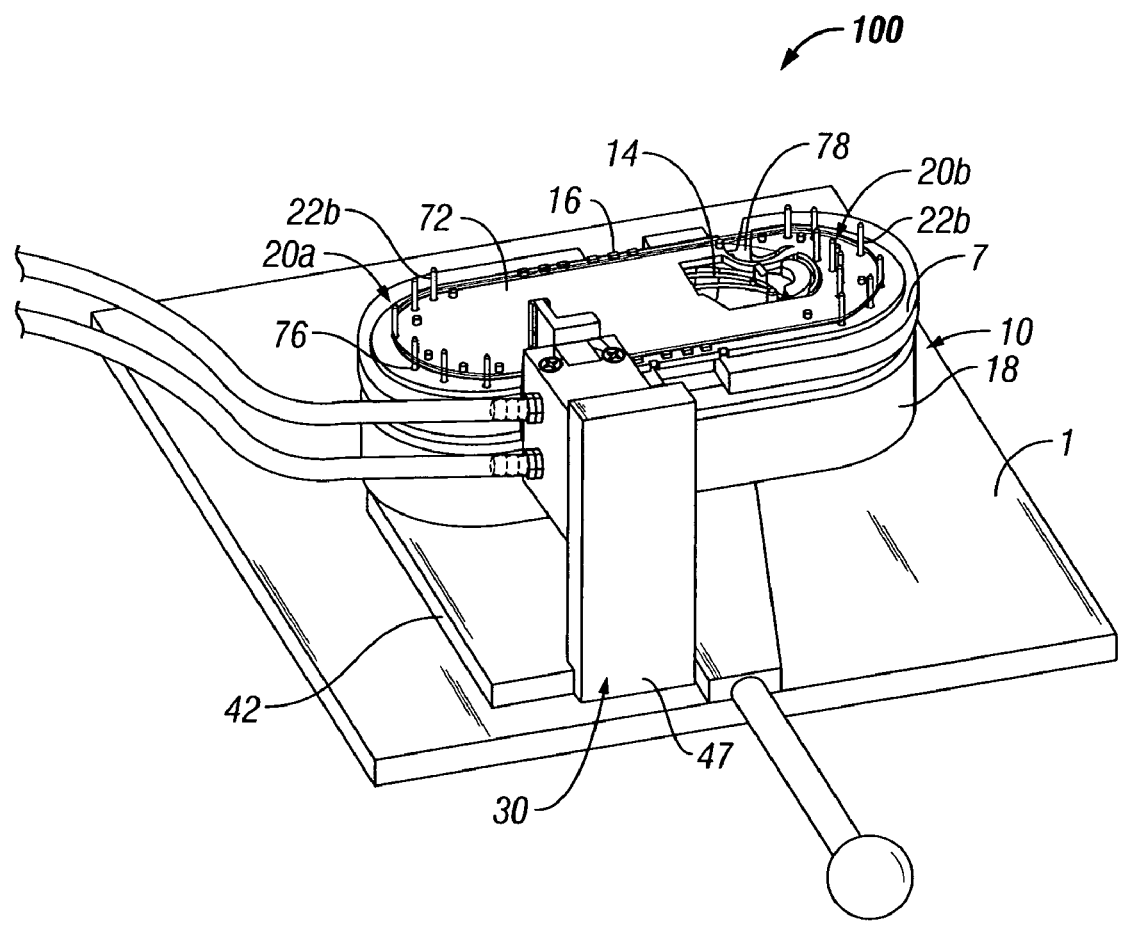
FIG. 7 is a perspective view of the suture winding device of FIG. 6 with the holder being in an unloading position.
Figure 8:
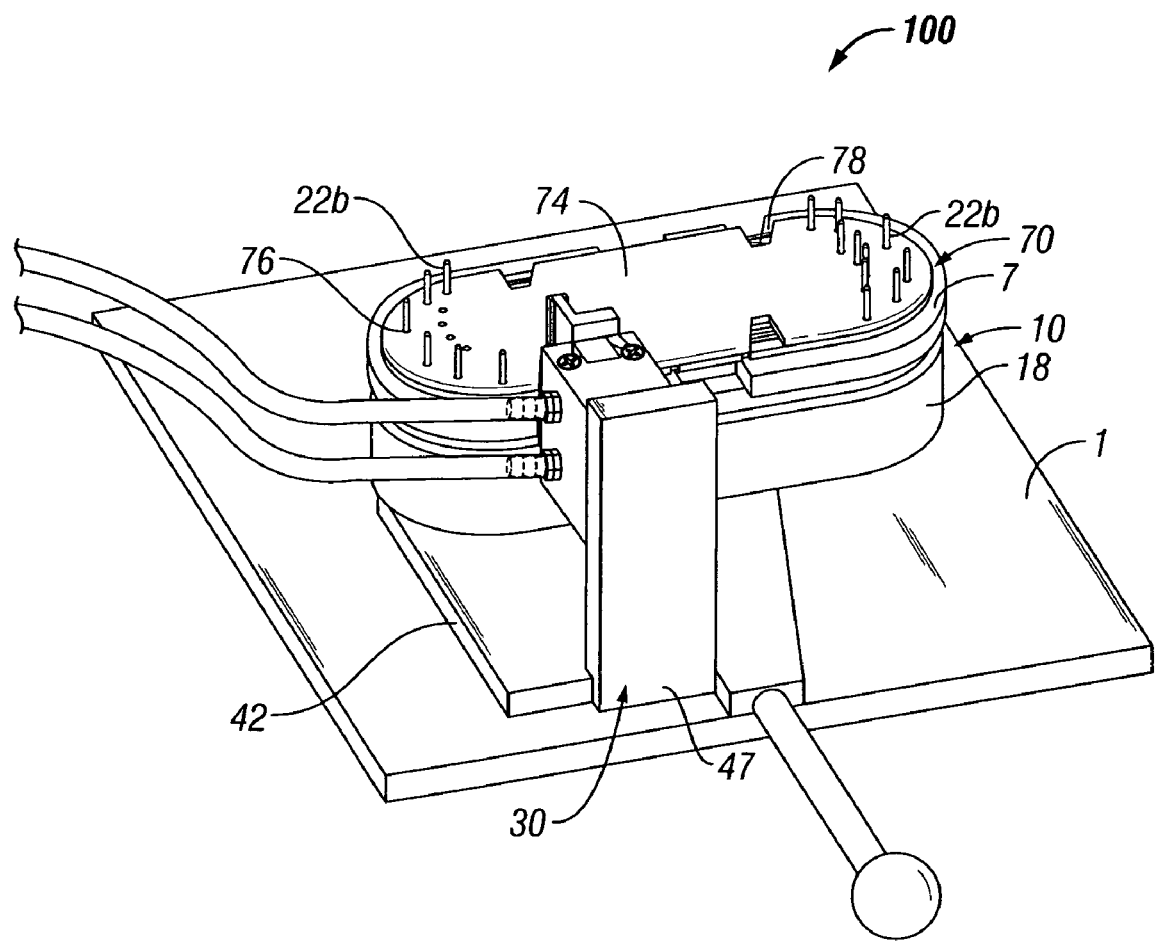
FIG. 8 is a perspective view of the suture winding device of FIG. 7 with a second member of the retainer positioned atop the first member of the retainer.

Base 10 is rotatable such that suture 16 contacts each exterior rod 22b sequentially. As base 10 completes each rotation, a loop of suture 16 is formed about exterior rods 22b. A predetermined amount of tension is maintained on suture 16 by a holder 30. Holder 30 is mounted to support plate 1 and is rotatable with respect to base 10. In one embodiment, holder 30 is rotatable amongst a plurality of positions including a loading position (FIG. 1) and an unloading position (FIG. 7). In addition, holder 30 is rotatable amongst the plurality of positions while base 10 is rotating about the central point (i.e. base 10 and holder 30 are independently positionable).

More specifically, holder 30 is attached to a mounting arm 42 (FIG. 1) that is rotatably attached to plate 1 and is capable of being positioned in at least the loading position and the unloading position of holder 30 and, preferably may be positioned in any position therebetween. Further still, mounting arm 42 is capable of being positioned independently of base 10.

Figure 6A:
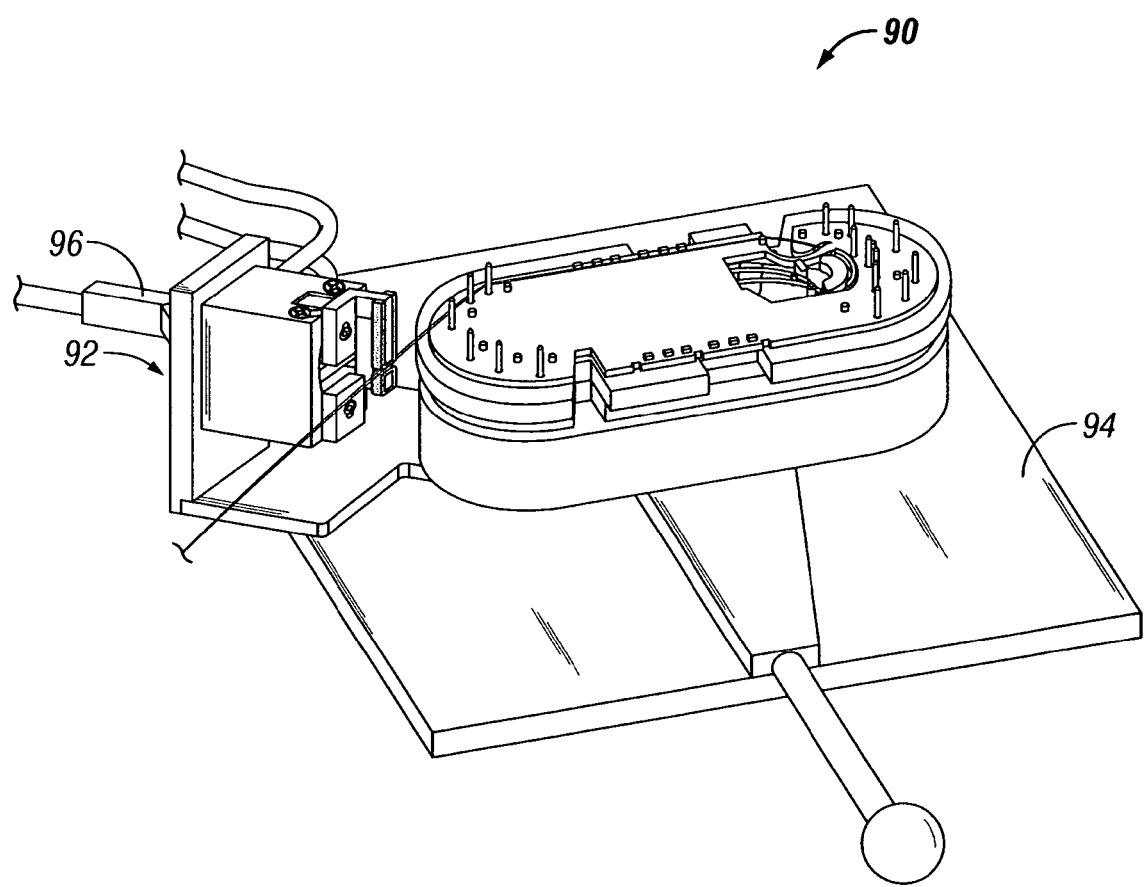
FIG. 6A is a perspective view of an alternate embodiment of the suture winding device of FIG. 5.

In a further embodiment, as seen in FIG. 6A, a suture winding device 90 includes a holder 92 that is rotatably attached to a plate 94 and movable through a plurality of positions, e.g. loading and unloading positions, as discussed above with respect to the embodiment depicted in FIGS. 1-7. In this embodiment, suture winding device 90 includes a programmable control module, actuator, or the like, generally designated by reference numeral 96, that is operatively connected to holder 92 such that movement through the plurality of positions may be either manually or automatically regulated.

Referring again to FIG. 6, in the loading position, holder 30 orients suture 16 such that a desired angle between suture 16 and base 10 is achieved. In the unloading position, holder 30 orients suture 16 such that it is substantially parallel to the longitudinal axis of base 10. The predetermined amount of tension applied to suture 16 is maintained by holder 30 regardless of its position relative to base 10 or whether or not base 10 is being rotated.

Figure 3:
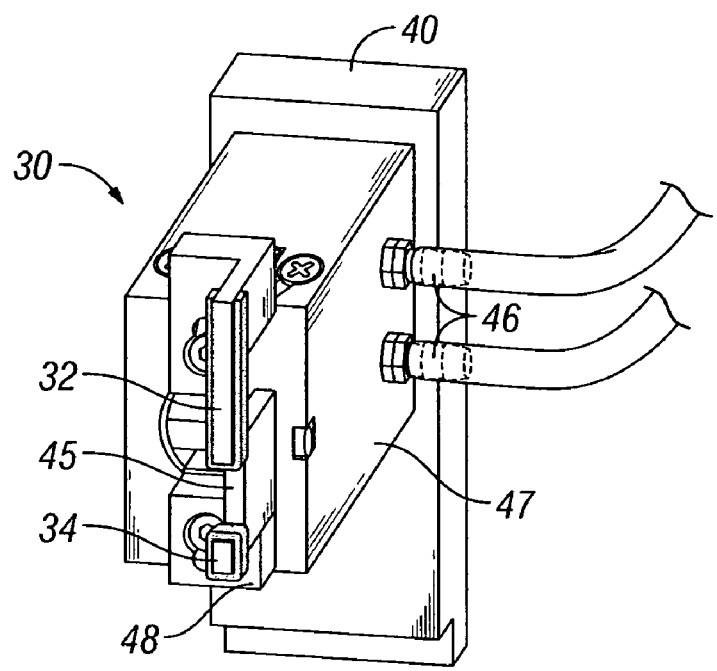
FIG. 3 is a side elevational view of the holder of FIG. 1 in a first state.
Figure 4:
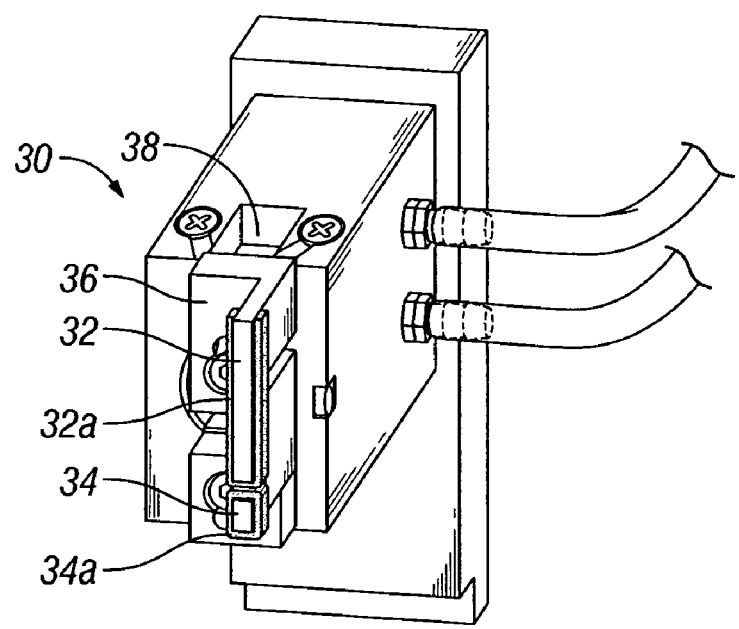
FIG. 4 is a side elevational view of the holder of FIG. 3 in a second state.

In particular and with reference to FIGS. 3 and 4, holder 30 includes a first arm 32 and a second arm 34. First arm 32 is movable such that holder 30 may transition between an open state and a closed state while second arm 34 is stationary. In particular, second arm 34 is fixedly attached to a block 48 that is, in turn, fixedly attached to a mounting block 47 that is attached to a wall 40.

Mounting block 47 includes an actuator and a slot 38 therein. Slot 38 is configured and dimensioned for slidably receiving a driver arm 36. First arm 32 is attached to driver arm 36 such that movement of driver arm 36 results in corresponding movement of first arm 32. In one embodiment, driver arm 36 is movable in slot 38 in a substantially vertical direction. In the open state, first arm 32 is spaced apart from second arm 34 defining a gap 45 therebetween (FIG. 3). Gap 45 has sufficient dimensions such that suture 16 may be fed through gap 45 without contacting either first or second arms 32, 34.

First arm 32 is moved towards second arm 34 during an actuation sequence such that first arm 32 substantially abuts second arm 34. In one embodiment, first and second arms 32, 34 may include respective first and second cushioning members 32a, 34a. During an actuation sequence, a pressure source is fluidly coupled to actuation ports 46 to provide the motive force to operate the actuator. Known pressure sources such as pneumatics (e.g. air, compressed gases, vacuum) or hydraulics (e.g. water, saline, oil) may be used with the actuator. In another embodiment, the actuator may be electrically powered by either AC or DC sources. Pneumatic, hydraulic, or electric actuators are well known to one skilled in this art and will not be discussed in detail herein.

Upon actuation, the actuator imparts motion to driver arm 36 to move driver arm 36 generally downward thereby transitioning it from its open state to its closed state. In the closed state, first arm 32 abuts second arm 34 and for slidably capturing a section of suture 16 therebetween. The amount of force exerted on suture 16 by first and second arms 32, 34 in the closed state is adjustable such that the amount of pressure applied is sufficient to allow suture 16 to be fed from a source to form the loops as base 10 rotates while maintaining the desired amount of tension on suture 16. Additionally, the amount of pressure applied by first and second arms 32, 34 minimizes drooping of a length of suture 16 extending between holder 30 and first member 72 when base 10 is stationary. By providing holder 30 to supply a predetermined amount of tension to suture 16 during the winding process, suture 16 is disposed within retainer 70 with a substantially uniform amount of applied tension. Additionally, holder 30, in cooperation with a uniform arrangement of rods 22, supplies the desired amount of tension to suture 16 during the winding process thereby distributing suture 16 in retainer 70 in a substantially uniform arrangement.

In an alternate embodiment, one or both of the first and second arms of the holder are movable relative to each other. In this embodiment, as the holder transitions from the open state to the closed state, the first arm may move toward the second arm, the second arm may move toward the first arm, or both arms may move towards each other. A programmable control module, actuator, or the like, may be operatively connected to one or both of the first and second arms of the holder such that the approximation thereof may be manually or automatically regulated.

Referring still to FIGS. 3 and 4, after the desired number of loops are formed (i.e. the desired quantity of suture 16 is disposed on first member 72 of retainer 70), rotation of base 10 is halted. Holder 30 is moved from the loading position to the unloading position while still maintaining the desired tension on suture 16. When holder 30 is in the unloading position, second member 74 is placed on top of first member 72, thereby forming retainer 70 and securing needle 14 and attached suture 16 within retainer 70. First arm 32 then transitions to its open state thereby releasing suture 16. Suture 16 is then separated from its source by known techniques such as cutting and a free end of suture 16 is positioned along a surface of first member 72. Alternatively, suture 16 may be separated from its source prior to transitioning first arm 32 to its open state. Throughholes 76 in second member 74 are arranged to correspond with and slidingly receive rods 22 thereby aligning first and second members 72, 74.

In one embodiment, first and second members 72, 74 are press fit together using applied pressure to engage corresponding edge portions of respective first and second members 72, 74 as is known in the art. In another embodiment, first and second members 72, 74 are joined together using a heat stake 110, such as those known in the art and illustrated in FIG. 9. Heat stake 110 includes a die plate 112 that is positionable along a vertical axis of heat stake 110. After retainer 70 is assembled (i.e. second member 74 is placed on top of first member 72), base 10 and retainer 70 are positioned such that die plate 112 is in substantial vertical alignment with retainer 70 by moving plate 1 along a horizontal set of rails or guides 122 that are mounted on plate 120. Plate 1, including base 10, is slidably attached to rails 122 using structures that are known in the art. In the alternative, base 10 may be stationary and heat stake 110 may be positionable along a horizontal set of rails or guides towards or away from base 10.

Figure 10:
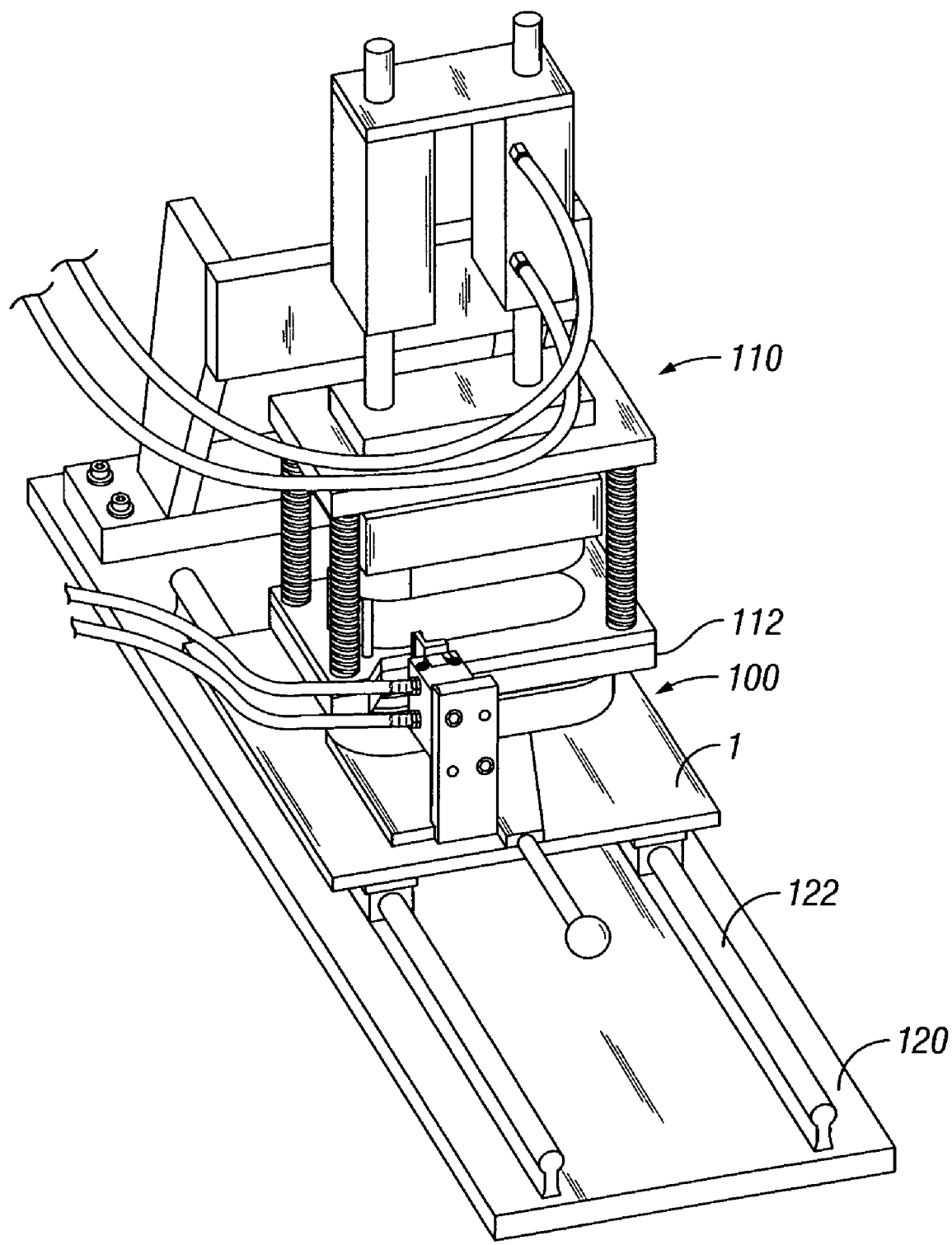
FIG. 10 is a perspective view of the suture winding device and the heat staking apparatus of FIG. 9 with a die plate positioned atop the retainer.

Once die plate 112 and base 10, particularly retainer 70, are vertically aligned (FIG. 10), one or both of base 10 or heat stake 110 is locked in position thereby maintaining the vertical alignment between retainer 70 and die plate 112. Die plate 112 includes at least one heating element as is known in the art such that when die plate 112 contacts second member 74 with a desired amount of pressure, a combination of the desired amount of pressure and/or thermal energy from the heating element joins first and second members 72, 74 to form retainer 70 (FIG. 10). In addition, die plate 112 includes a plurality of channels or tubes (not shown) configured and arranged for slidably receiving rods 22. After first and second members 72, 74 are joined to form retainer 70, die plate 112 separates from base 10 (FIG. 11) allowing movement of plate 1 and removal of retainer 70 from base 10.

A method of winding a needle or an armed needle using the hereinabove described suture winding device 100 will now be discussed in detail. With reference initially to FIG. 5, one or more needles 14 having a quantity of suture 16 attached thereto is positioned in needle holder 50. Specifically, each needle 14 is positioned in a separate needle channel 64 and attached suture 16 is threaded between interior rods 22a and exterior rods 22b such that suture 16 is positioned between at least one interior rod 22a and at least one exterior rod 22b. After threading suture 16 between interior and exterior rods 22a, 22b, suture 16 extends beyond a top surface of mounting member 7. First member 72 of retainer 70 is placed on mounting member 7 such that rods 22 align with throughholes 76. Since rods 22 and throughholes 76 are configured for slidably engaging one another, a minimum amount of downward force is applied to position first member 72 in contact with the top surface of mounting member 7. Suture 16 extends through slot 78 of first member 72 and is accessible from a region exterior to base 10.

Once first member 72 of retainer 70 is positioned on mounting member 7, vacuum may be applied through vacuum ports 12a thereby holding first member 72 in substantial contact with the top surface of mounting member 7. Suture 16 is placed between first and second arms 32, 34 of holder 30 while first arm 32 is in the open state (FIG. 3). After placing suture 16 between first and second arms 32, 34, the actuator is energized by the selected power source (i.e. pneumatic, hydraulic, or electric) to transition first arm 34 from the open state to the closed state and slidably capturing a portion of suture 16 therebetween.

Base 10 is rotated as suture 16 is fed from a source (not shown) thereby winding a quantity of suture 16 around rods 22 forming loops of suture 16. After a desired quantity of suture 16 is disposed on first member 72, rotation of base 10 is halted. Holder 30 is then positioned from its loading position shown in FIG. 6 to its unloading position in FIG. 7. By maintaining suture 16 between arms 32 and 34 of holder 30 as it transitions from its loading position to its unloading position, a desired amount of tension is maintained on suture 16 prior to joining first and second members 72, 74 of retainer 70. The desired quantity of suture 16 that is disposed on first member 72 may then be separated from the source of suture 16 by cutting or other techniques known in the art. The separated end of suture 16 is positioned along the top surface of first member 72 prior to placing second member 74 atop first member 72.

Figure 9:
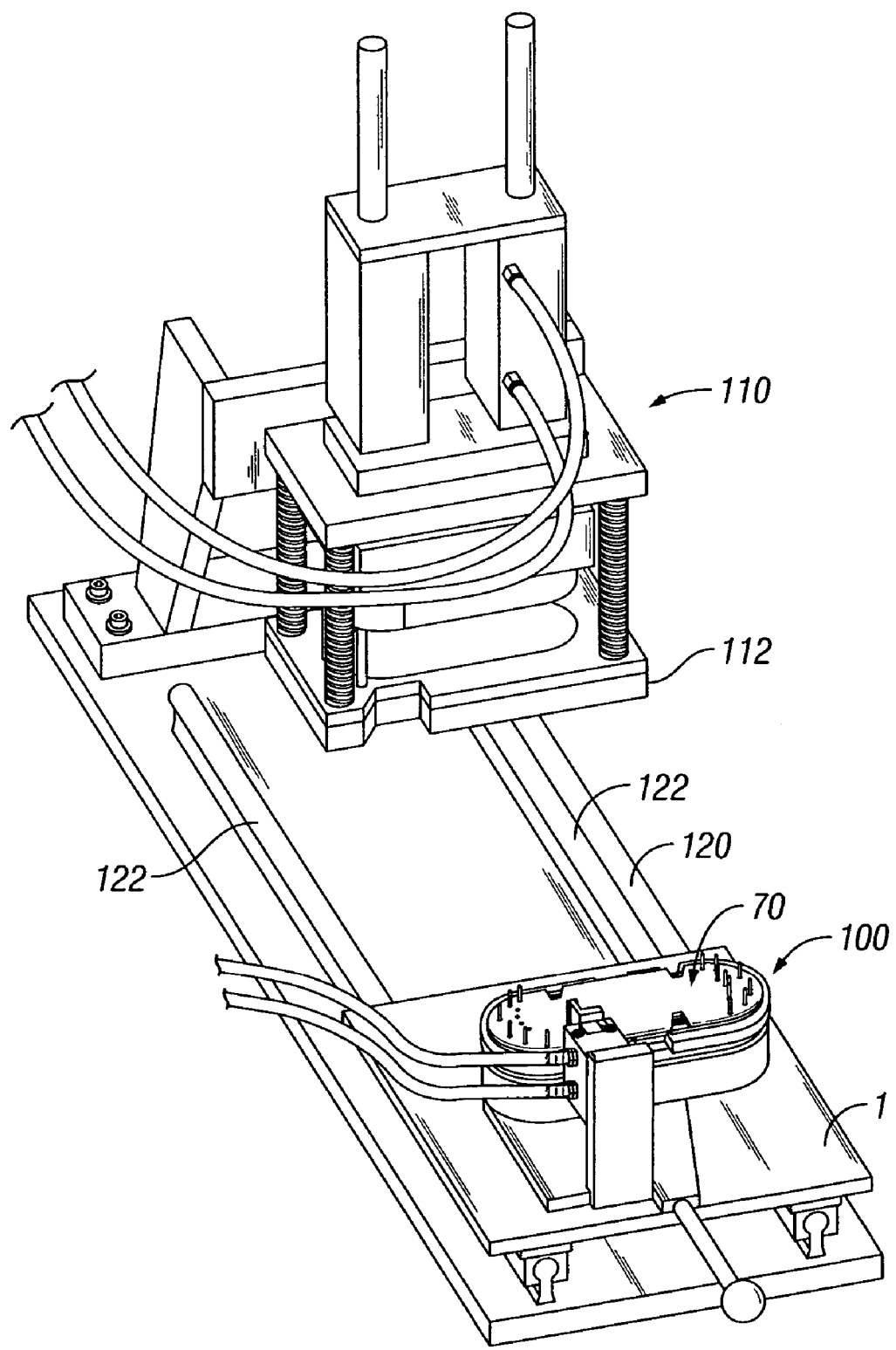
FIG. 9 is a perspective view of the suture winding device of FIG. 8 and a heat staking apparatus.

After second member 74 is positioned on top of first member 72, pressure and/or heat may be used to form retainer 70 by joining first and second members 72, 74. As seen in FIG. 9, the assembled retainer 70 sits atop base 10 and plate 1. Plate 1 may be moved along rails 122 for positioning plate 1 and base 10 in alignment with die plate 112 such that vertical movement of die plate 112 will contact second member 74 of retainer 70 to apply a desired amount of pressure and/or thermal energy to join first and second members 72, 74 (FIG. 10). Channels (not shown) in die plate 112 slidably receive rods 22 as die plate 112 contacts second member 74. After joining first and second members 72, 74, die plate 112 is moved away from base 10 in a generally vertical direction (FIG. 11) such that base 10 and retainer 70 may be moved along rails 122. Retainer 70 is now formed and includes needle 14 and the desired quantity of suture 16. The steps are repeatable for each retainer 70 to be formed.

Referring now to FIGS. 12A-13B, in another embodiment, an apparatus 200 for packaging a suture 216 includes a base member 210, at least one rod 222 arranged in at least one array 220, a retainer package 270, and a holder 230 having first and second arms (not shown). Each of these elements is substantially similar to those described above with respect to the previous embodiments and have been renumbered accordingly. For the sake of brevity, only the differences between the embodiments will be discussed in detail. In this embodiment, apparatus 200 further includes a parking mechanism 240 and at least one positioning rod 260.

Parking mechanism 240 maintains a pre-determined orientation of a tail portion 216a of suture 216 during the winding process, as discussed in further detail below, and includes an attachment member 242 and first and second arms 244, 246, respectively.

Attachment member 242 is any plate, strut, rod, or other structure suitable for the intended purpose of associating parking mechanism 240 with apparatus 200. In the embodiment depicted in FIGS. 12A-12B, attachment member 242 is fixedly supported on a heat stake apparatus 280 similar to that which was discussed above with respect to the embodiment depicted in FIGS. 9-11. The attachment member 242 may be movably supported on the heat stake apparatus 280. Additionally, the attachment member 242 may be either fixedly or movably supported to the apparatus 200 itself at any suitable location, e.g. the base member 210, or to any other structure suitable for the intended purpose of facilitating the operation of the parking mechanism 240, as described in further detail below.

Figure 12A:
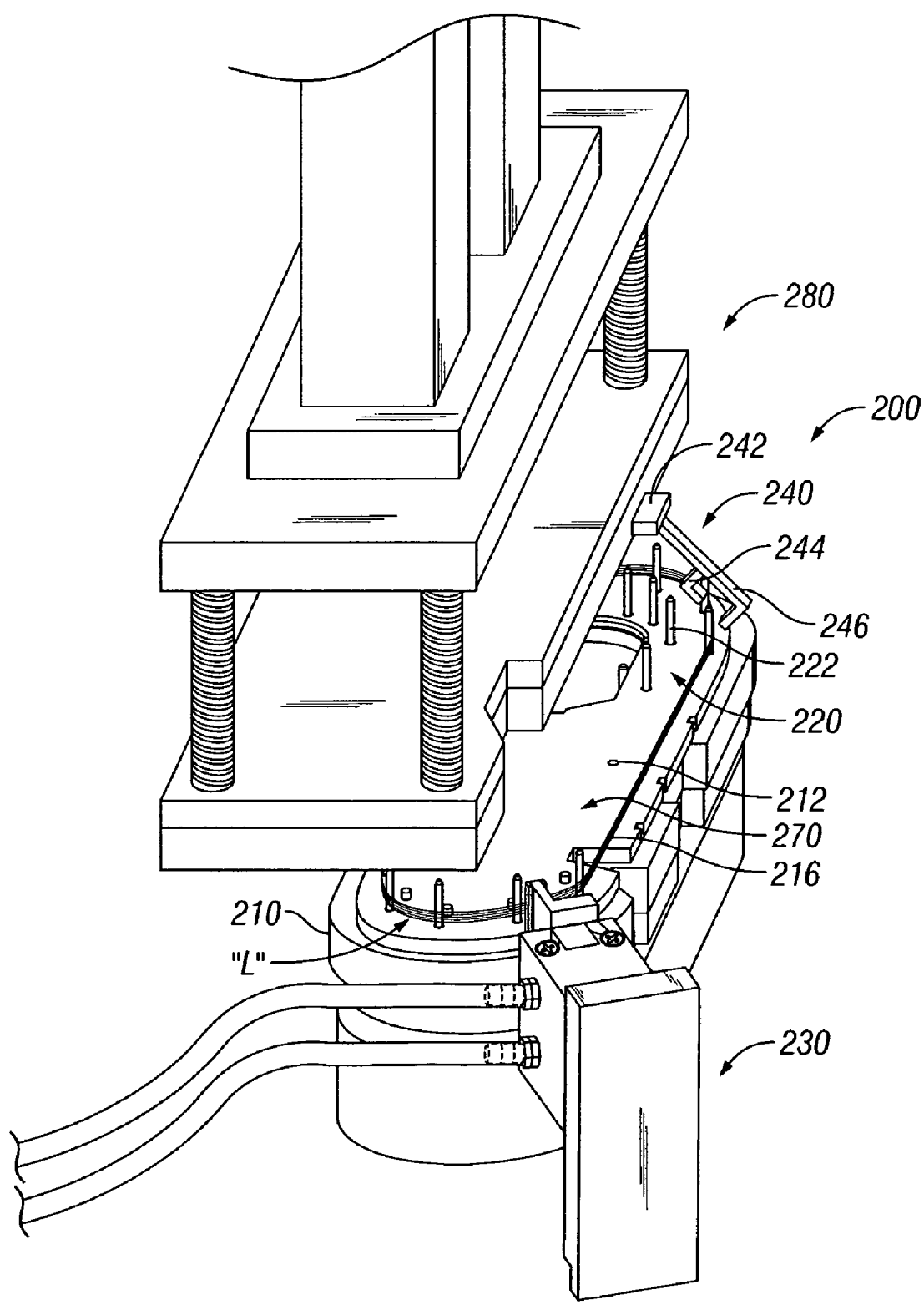
FIG. 12A is a perspective view of another embodiment of the suture winding device and the heat staking apparatus of FIG. 10 including a parking mechanism in a first position.
Figure 12B:
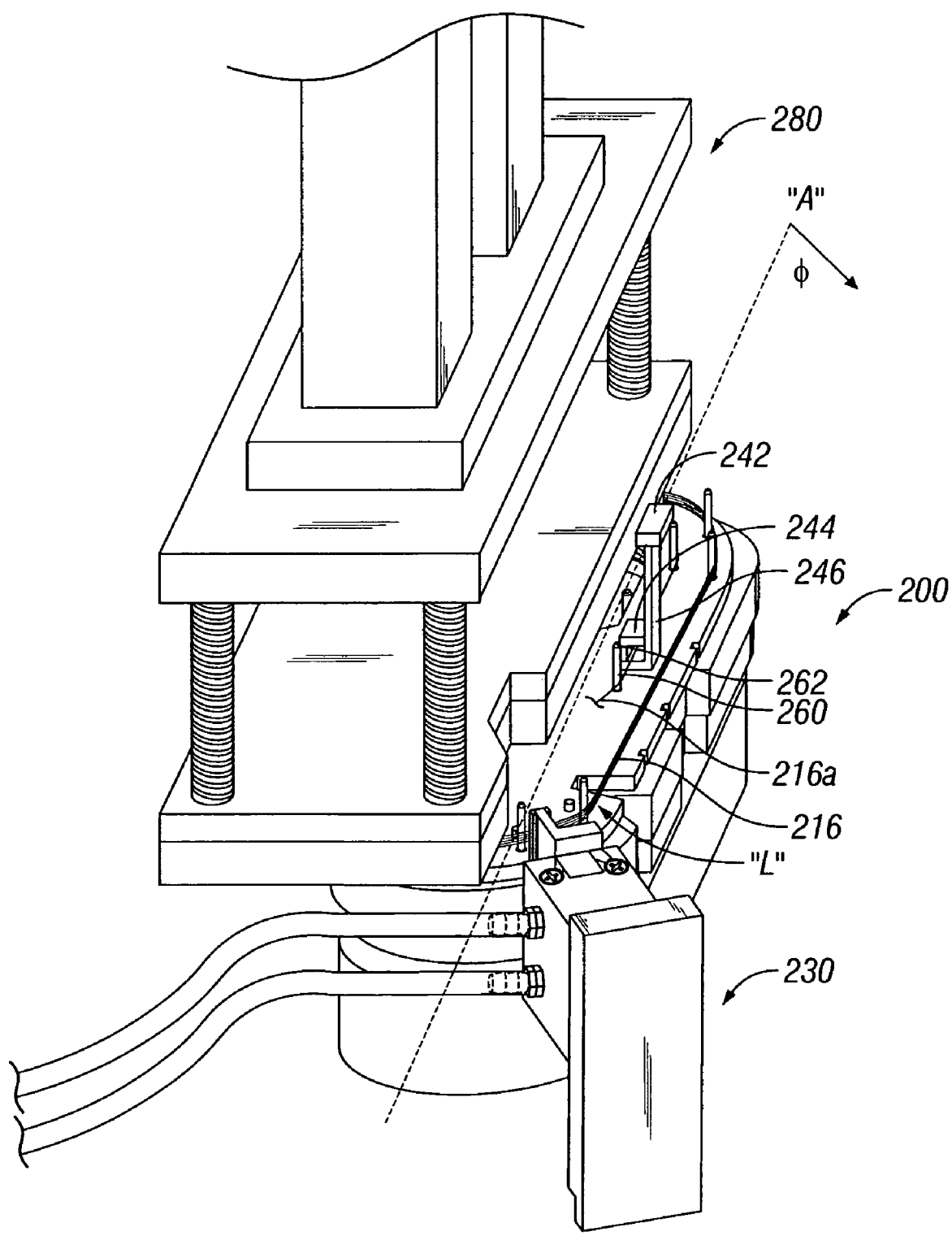
FIG. 12B is a perspective view of the suture winding device of FIG. 12A in a subsequent position.

Referring still to FIGS. 12-12B, second arm 246 is movably connected to attachment member 242 such that parking mechanism 240 is free to pivot, rotate, slide, or the like, between a first position (FIG. 12A) and at least one subsequent position (FIG. 12B). Movement of parking mechanism 240 between the first position and the at least one subsequent position may be facilitated through any suitable structural mechanism, e.g., a hinge or a pivot.

In the first position (FIG. 12A), parking mechanism 240 is oriented so as not to engage suture 216. In the at least one subsequent position (FIG. 12B), parking mechanism 240 is reconfigured to facilitate engagement with at least a portion, e.g. tail portion 216a, of suture 216, as described in further detail below. The parking mechanism may be operatively associated with a programmable control module, actuator, or the like, such that movement from the first position to the at least one subsequent position may be manually or automatically regulated.

Alternatively, the attachment member may be fixedly attached to the apparatus such that the radial, lateral, or rotational movement of the parking mechanism is substantially prevented. As such, the parking mechanism remains substantially stationary and, accordingly, does not transition between the first and second positions discussed above.

Parking mechanism 240 includes respective first and second arms 244, 246. In one embodiment, first arm 244 is movable in relation to second arm 246 such that parking mechanism 240 may transition between an open condition (FIG. 13A) and a closed condition (FIG. 13B), while second arm 246 is stationary.

Second arm 246 includes a slot 248 defined therein that is configured and dimensioned to slidably receive a portion of first arm 244. In the open condition, first arm 244 is spaced apart from second arm 246 such that a space 250 is defined therebetween that is dimensioned to receive at least a portion of suture 216, e.g. tail portion 216a. First arm 244 is approximated relative to second arm 246 during an actuation sequence until first arm 244 substantially abuts second arm 246, thereby closing off space 250 in the closed condition, and releasably retaining tail portion 216a of suture 216 therein.

In another embodiment, the parking mechanism may be operatively connected to a programmable control module, actuator, or the like such that the transition from the open condition to the closed condition may be manually or automatically regulated.

Figure 13A:
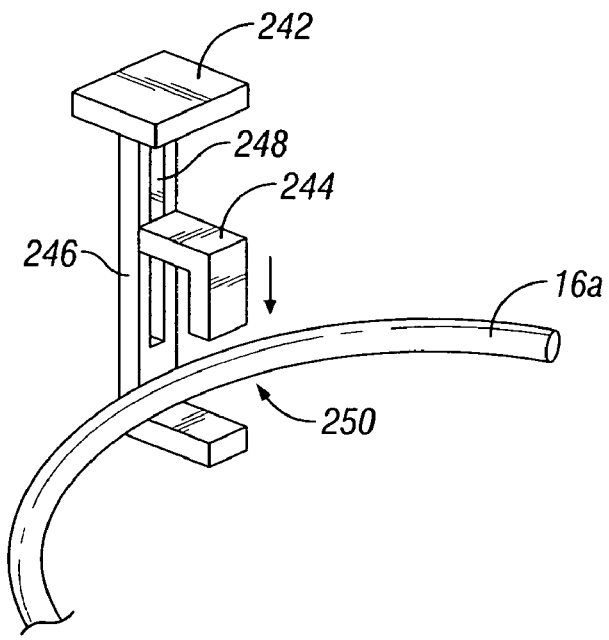
FIG. 13A is a side perspective view of the parking mechanism of FIGS. 12A-12B showing the parking mechanism in an open condition.
Figure 13B:
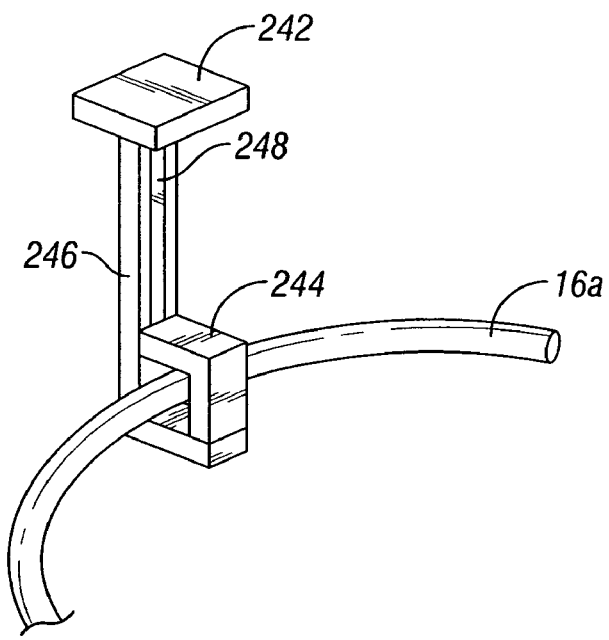
FIG. 13B is a side perspective view of the parking mechanism of FIGS. 12A-12B showing the parking mechanism in a closed condition.

As seen in FIGS. 12B and 13B, when parking mechanism 240 is in the second position and the closed condition, tail portion 216a of suture 216 in oriented and maintained in desired, pre-determined manner with respect to base member x defined by angle $\Phi$, as discussed in further detail below. Angle $\Phi$ may be any angle substantially within the range of 0° to 180°.

In one embodiment, the present disclosure contemplates that both the first and second arms of the parking mechanism are movable. As the parking mechanism transitions from the open condition to the closed condition, the first and second arms approximate relative to one another.

As indicated above, apparatus 200 also includes at least one positioning rod 260 that is extendable at least partially through an aperture 212 formed in base member 210 and retainer package 270. Positioning rod 260 includes a tip 262 and is movable from a first or retracted position, seen in FIG. 12A, in which tip 262 is substantially flush with or below base member 210, to a second or extended position, seen in FIG. 12B, in which positioning rod 260 is configured to engage tail portion 216a of suture 216. In the extended position, positioning rod 260 ensures that tail portion 216a remains in the predetermined orientation, as discussed above, until assembly of the retainer package 270 is complete. In one aspect of the present disclosure, the parking mechanism and the positioning rod cooperate to orient the tail portion of the suture within a perimeter of the retainer package.

The positioning rods may be operatively connected to a programmable control module, actuator, or the like, such that the transition of the positioning rod between the first or retracted position and the second or extended position may be either manually or automatically regulated.

A method of winding a suture 216 using apparatus 200 will be discussed. Prior to the formation of loops "L" of suture 216 about rods 222, the method described hereinbelow is substantially identical to that which was discussed above, and will therefore not be repeated. During and immediately prior to the formation of loops "L", parking mechanism 240 is in the first position (FIG. 12A) and in the open condition (FIG. 12B). Subsequent to the formation of loops "L", parking mechanism 240 transitions both into the second position (FIG. 12B), so at to facilitate engagement with tail portion 216a of suture 216, and the closed condition (FIG. 13B), thereby releasably capturing tail portion 216a within space 250.

After positioning parking mechanism 240 in the second position and the closed condition, positioning rod 260 is extended from the retracted position (FIG. 12A), such that tip 262 extends at least partially beyond base 210, thereby facilitating engagement of positioning rod 260 with tail portion 216a of suture 216. In the extended position, positioning rod 260 cooperates with parking mechanism 240 to configure tail portion 216a of suture 216 in the pre-determined orientation, as discussed above.

Figure 14A:
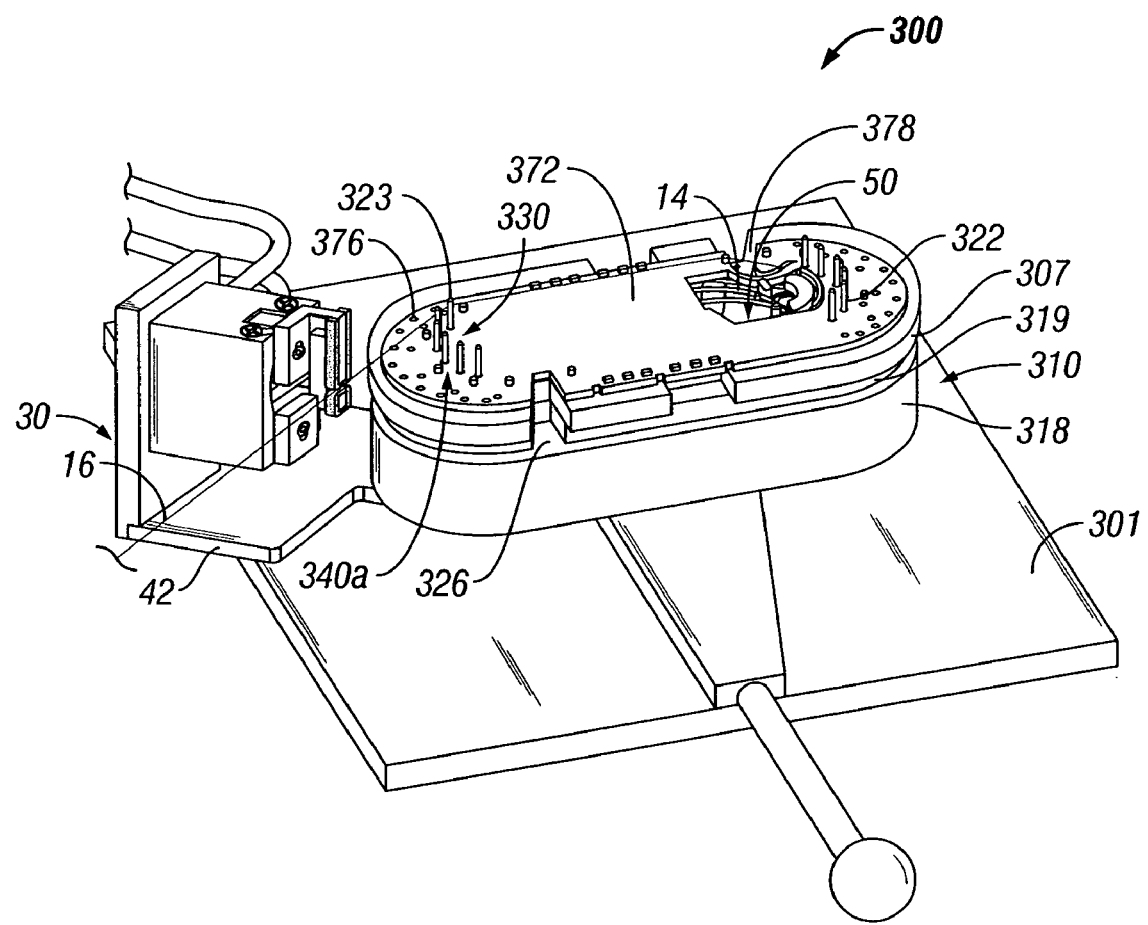
FIG. 14A is a perspective view of another embodiment of the presently disclosed suture winding device with an embodiment of the holder in the loading position and a first array of rods in a second position.
Figure 14B:
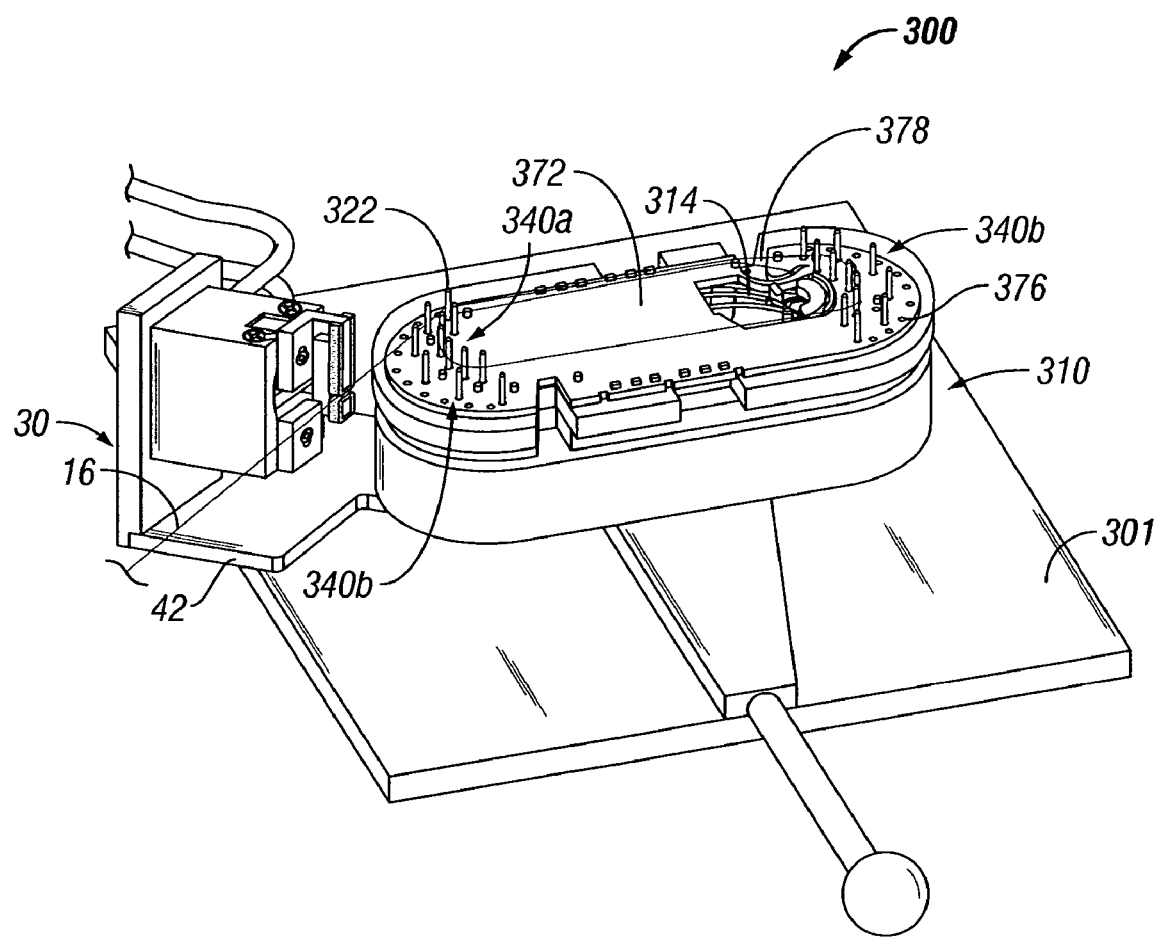
FIG. 14B is a perspective view of the suture winding device of FIG. 14A showing a second array of rods in the second position.
Figure 14C:
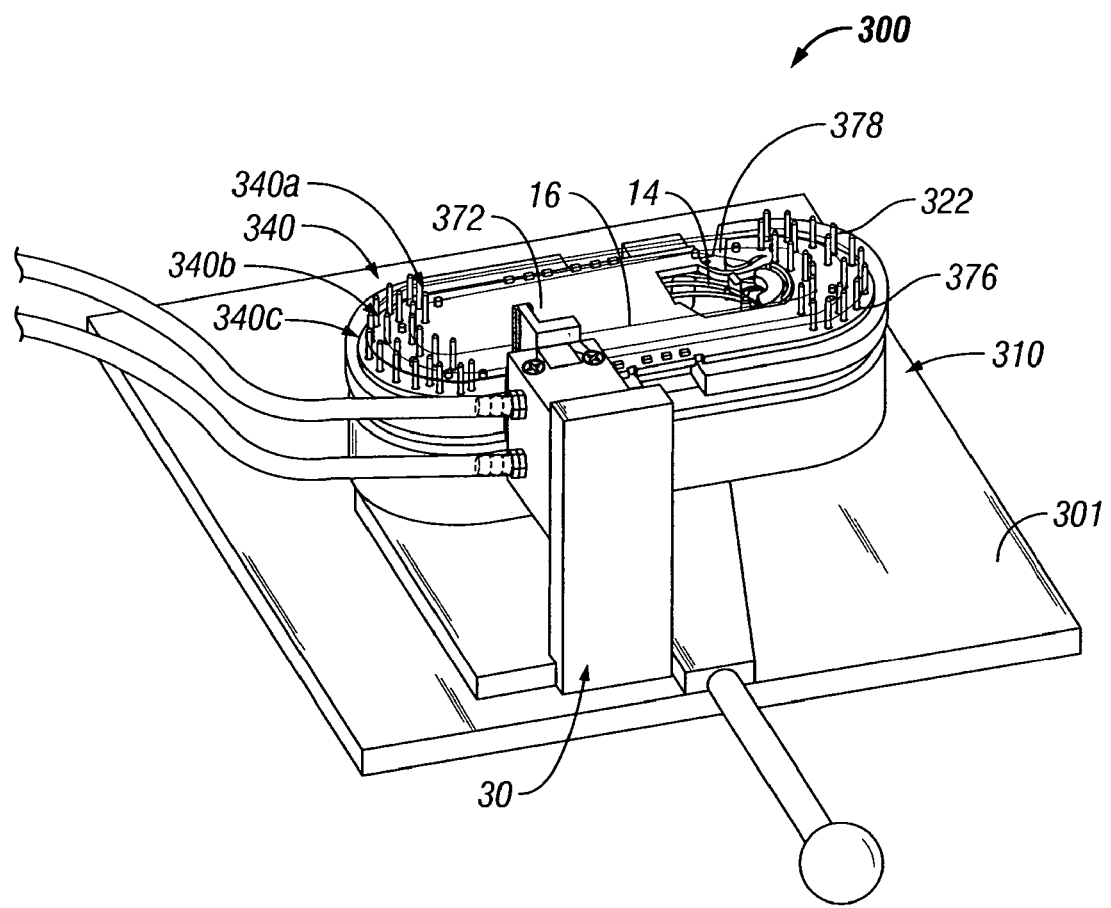
FIG. 14C is a perspective view of the suture winding device of FIG. 14B showing a third array of rods in the second position and the holder in the unloading position.

Referring now to FIGS. 14A-14C, another embodiment of the suture winding device is illustrated and shown generally as 300. Suture winding device 300 includes a base 310 that is rotatably mounted to a plate 301. Holder 30, that was discussed in detail previously with reference to FIGS. 3-4, is rotatably mounted to plate 301. Base 310 is a generally elliptical structure that includes a frame 318 and a plate 319 that is attached to a mounting surface 326 of frame 318. A mounting member 307 is disposed atop plate 319 and provides a surface suitable for positioning a first member 372 of a retainer. Mounting member 307 includes needle holder 50 as previously shown and described with reference to FIG. 2. As in the previous embodiment, needle 14 has a quantity of suture 16 attached thereto and is disposed in needle holder 50. A portion of suture 16 extends beyond base 310 and is threaded through first and second arms 32, 34 of holder 30.

Suture winding device 300 includes a plurality of rods 322 that is extendable through throughholes 376 of first member 372 where each rod 322 includes a tip 323. In this embodiment, rods 322 are positionable between a first or retracted position and a second or extended position as shown in FIGS. 14A-14C. It is contemplated that the suture winding device may include a programmable control module, an actuator, or the like, operatively connected to the rods such that the transition between the first or retracted position and the second or extended position may be either manually or automatically regulated. When in the extended position, rods 322 are capable of forming one or more loops of suture 16 as will be discussed in detail hereinbelow. In the retracted position, tips 323 of rods 322 are substantially flush with a top surface of mounting member 307. Alternatively, tips 323 may exist below the top surface of mounting member 307. In addition, rods 322 are arranged in one or more arrays 330. Each array 330 includes a plurality of rods 322 that are arranged in one or more arcs 340 of rods 322. Furthermore, in an embodiment having two arrays 330, the arrays 330 are spaced apart along a longitudinal axis of base 310. Similar to suture winding device 300, arrays 330 are spaced apart about needle holder 50. Needle holder 50 is releasably mounted in mounting member 307 such that a top surface of plate 52 is substantially flush with the top surface of mounting member 307. As in the previous embodiment, needle holder 50 may be replaced by alternate embodiments of the needle holder that are configured to receive single needles, double needles, or needles of varying diameters and dimensions regardless of whether the needles are in a single or double configuration.

In FIG. 14A, rods 322 are shown in the extended position and each array 330 includes an arc 340 of rods 322. Additional arcs 340 are illustrated in FIGS. 14B-14C. In FIG. 14B, each array 330 includes two arcs (340a, 340b) while FIG. 14C illustrates suture winding device 300 with three arcs (340a, 340b, 340c) in each array 330. The spatial arrangement and relationship of rods 322, arrays 330, and arcs 340 will now be discussed in further detail. Moving from needle holder 50 towards an outer edge of mounting member 307, arcs 340 have successively larger radii such that rods 322 in arc 340a (i.e. closest to needle holder 50) are spaced closer together than rods 322 in arc 340b (FIG. 14B). In an embodiment including three arcs (FIG. 14C), arc 340c is spaced further away from needle holder 50 than arc 340b and has a larger radii than arc 340b or 340a such that rods 322 in arc 340c are spaced further apart than rods 322 in arc 340a or 340b. In addition, in configurations using more than three arcs, the radius of each arc increases as each arc is spaced further away from needle holder 50 towards the outer edge of mounting member 307 thereby increasing the distance between rods 322 in each arc.

As previously mentioned, rods 322 are positionable between a retracted position and an extended position. Each rod 322 may be independently positionable. In one embodiment, rods 322 in each arc (340a, 340b, or 340c) are positionable as a group such that all rods 322 in each arc (340a, 340b, or 340c) move substantially simultaneously. In addition, in embodiments having two arrays 330, arcs may be positioned sequentially such that rods 322 in arc 340a are moved substantially in unison from the retracted state to the extended state or vice versa. Furthermore, additional arcs 340b, 340c are positioned similarly such that corresponding arcs in each array 330 (i.e. arc pairs 340a, 340a or 340b, 340b or 340c, 340c) are moved substantially simultaneously.

Operative force to transition rods 322 from the retracted to the extended position or the extended to the retracted position may be supplied by mechanical, hydraulic, pneumatic, or electric sources as are well known to those of skill in the art. In one embodiment, rods 322 are transitioned from their positions using a number of cams and/or levers. Alternately, hydraulic force supplied by water or oil, pneumatic force supplied by air or other compressed gasses, or electric force supplied by motors or solenoids may be substituted for or combined with the cams and/or levers.

A method of winding a needle or an armed needle using the hereinabove described suture winding device 300 will now be discussed in detail. With reference initially to FIG. 14A, each array 330 has rods 322 of arc 340a in their extended position. One or more needles 14 having a quantity of suture 16 attached thereto is positioned in needle holder 50 as discussed in detail above with reference to FIG. 5 and first member 372 is placed on mounting member 307 such that rods 322 in the extended position align with throughholes 376. Since rods 322 and throughholes 376 are configured for slidably engaging one another, a slight amount of downward force is required to position first member 372 in contact with the top surface of mounting member 307. Suture 16 extends through slot 378 of first member 372 such that it is accessible from an outside region. Subsequently, suture 16 is positioned such that a portion of suture 16 contacts one or more of rods 322 in arc 340a.

Suture 16 is then placed between first and second arms 32, 34 of holder 30 while first arm 32 is in the first state (FIG. 3). After placing suture 16 between first and second arms 32, 34, the actuator is energized by the selected power source (i.e. pneumatic, hydraulic, or electric) to transition first arm 34 from the first state to the second state (i.e. towards second arm 34) and slidably capturing a portion of suture 16 therebetween.

Base 310 is rotated on plate 301 such that a desired quantity of suture 16 is wound about rods 322 in arcs 340a forming loops of suture 16 (FIG. 14A). After one or more loops are formed about arcs 340a, rods 322 in arcs 340b may be transitioned to their extended position (FIG. 14B) while base 310 continues to rotate on plate 301 and rods 322 in arcs 340a remain in their extended position. Once rods 322 of arcs 340b are transitioned to their extended positions, suture 16 now forms loops only about arcs 340b without forming additional loops about arcs 340a. After one or more loops of suture 16 are formed about arcs 340b, rods 322 in arcs 340c may be transitioned to their extended position (FIG. 14C) while base 310 continues to rotate. As base 310 rotates, one or more loops of suture 16 are only formed about arcs 340c without forming additional loops about arcs 340a or 340b. While loops of suture 16 are forming about arcs 340c, rods 322 in arcs 340a and 340b remain in their extended position maintaining the previously formed loops of suture 16.

After a desired quantity of suture 16 is disposed on first member 72, rotation of base 310 is halted. Holder 30 is then positioned from its loading position shown in FIG. 14A to its unloading position in FIG. 14C. By maintaining suture 16 between arms 32 and 34 of holder 30 as it transitions from its loading position to its unloading position, a desired amount of tension is maintained on suture 16 prior to forming retainer 70. The desired quantity of suture 16 that is disposed on first member 372 may then be separated from the source of suture 16 by cutting or other techniques known in the art. The separated end of suture 16 is positioned along the top surface of first member 372 prior to placing a second member of retainer atop first member 372 similar to the formation of retainer 70 in the previously discussed embodiment.

Figure 11:
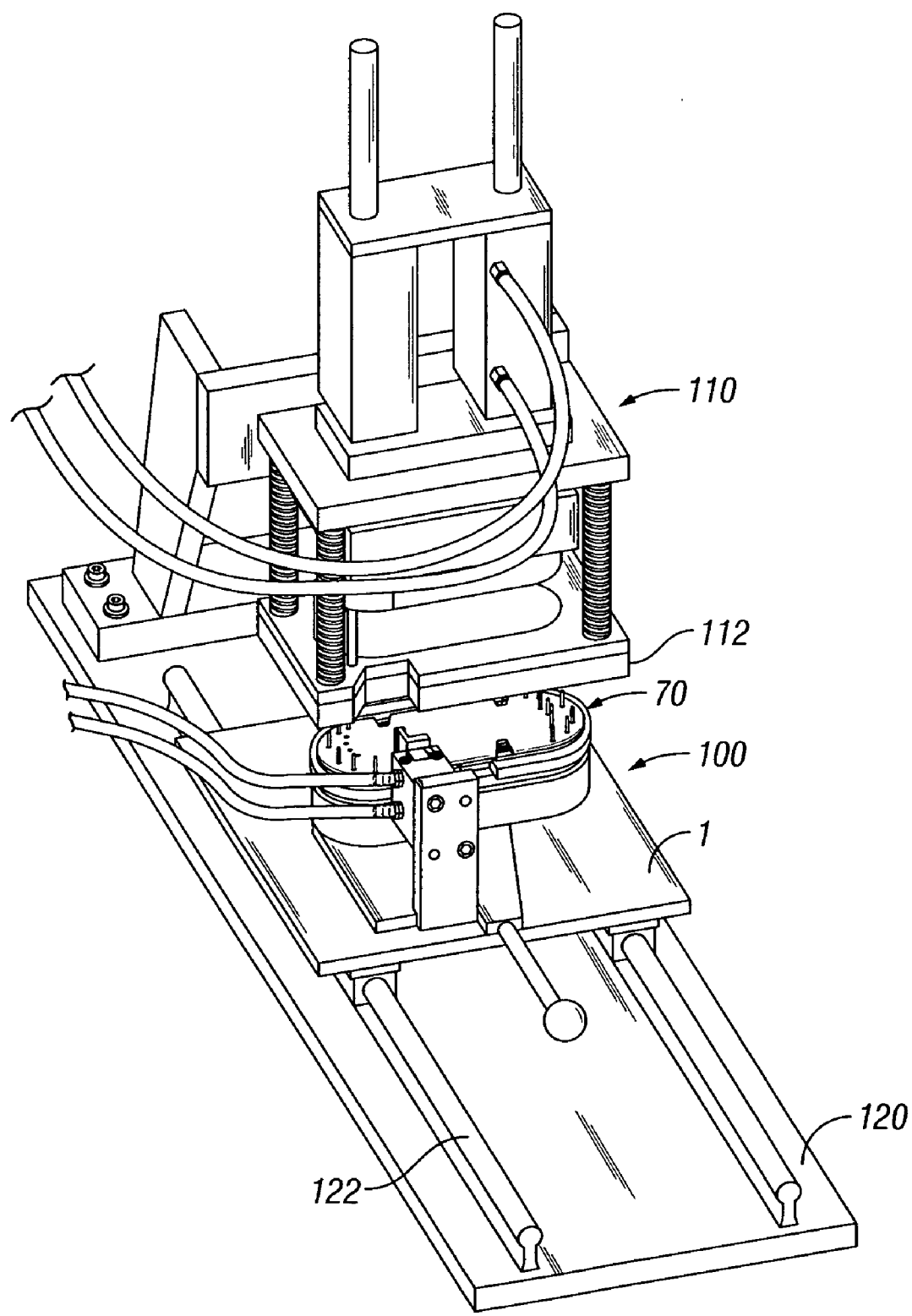
FIG. 11 is a perspective view of the suture winding device and the heat staking apparatus of FIG. 10 after assembly of the retainer.

Joinder and formation of retainer 70 is substantially similar to that of the previous embodiment using pressure and/or thermal energy from heat stake apparatus 110 as illustrated in FIGS. 9-11 and discussed previously.

Figure 15:
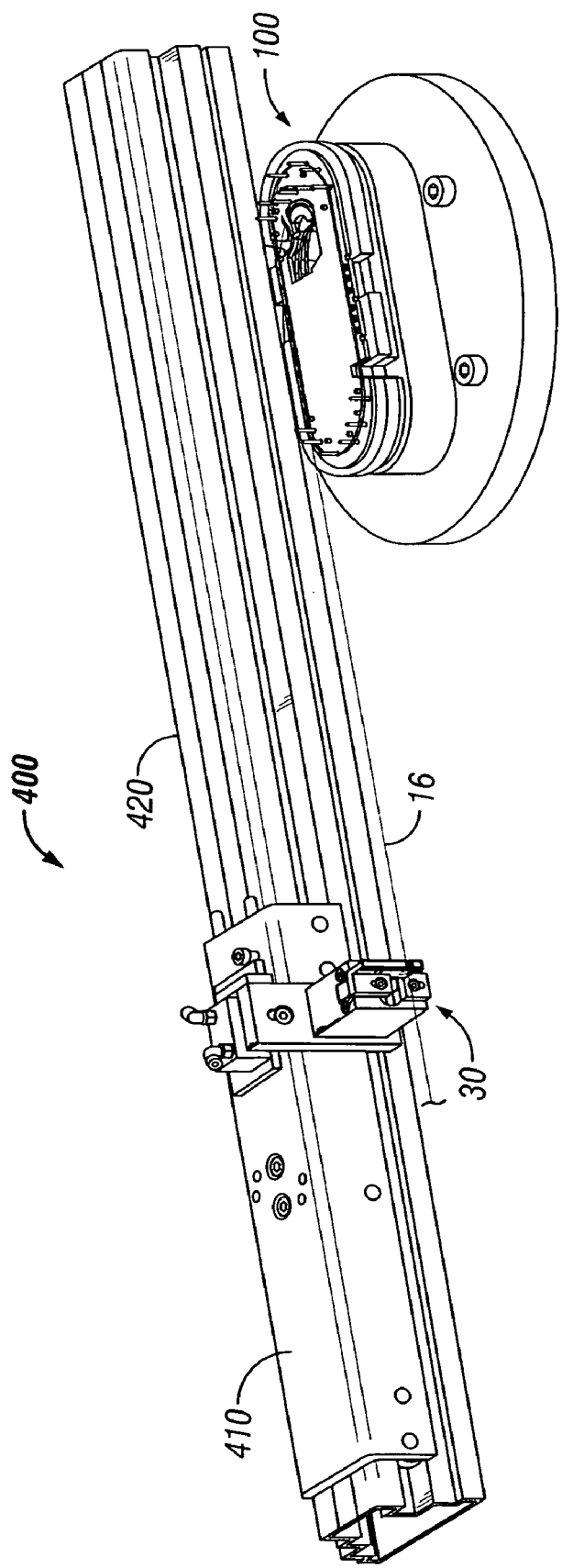
FIG. 15 is a perspective view of the presently disclosed suture winding device and another embodiment of a holder shown in a loading position.

In another embodiment, holder 30 is attached to a rail assembly 400 as shown in FIGS. 14-15. Holder 30 was previously described with reference to FIGS. 3-4. In this embodiment, holder 30 is positionable on rail assembly 400 rather than being rotatably mounted to plate 1 using mounting arm 42 as in the previous embodiment.

Figure 16:
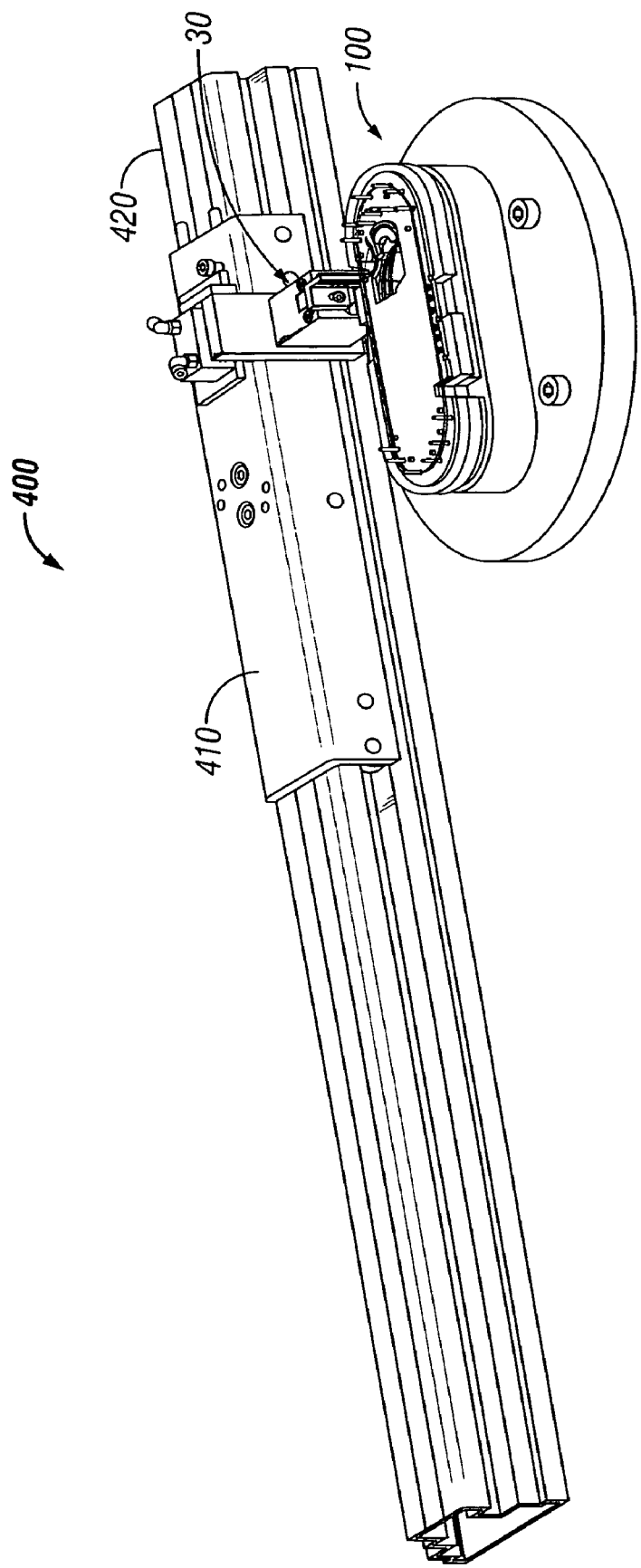
FIG. 16 is a perspective view of the suture winding device and holder of FIG. 15 shown in an unloading position.

Rail assembly 400 includes a carriage 410 that is slidably mounted to rail 420 using structures and techniques known to those of skill in the art. Holder 30 is attached to carriage 410 thereby allowing holder 30 to be positioned along rail 420 throughout a plurality of positions including a loading position (FIG. 15) and an unloading position (FIG. 16). Holder 30 and rail assembly 400 are adapted for use with any of the embodiments disclosed herein, i.e. suture winding device 100 is shown in FIGS. 15-16 for illustrative purposes only.

As suture 16 is wound onto suture winding device 100, as previously shown and described, carriage 410 and holder 30 move along rail 420 from the loading position to the unloading position. Movement of carriage 410 is coordinated and synchronized with the rotation of suture winding device 100 such that the desired amount of tension is maintained on suture 16 during the winding process. After the desired amount of suture 16 is wound onto suture winding device 100 (i.e. holder 30 is in the unloading position), suture 16 may be separated as discussed previously with reference to suture winding device 100.

Joinder and formation of retainer 70 is substantially similar to that of the previous embodiment using pressure and/or thermal energy from heat stake apparatus 110 as illustrated in FIGS. 9-11 and discussed previously.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An apparatus for winding a suture comprising:
    a support member;
    a base member attached to the support member and defining a longitudinal axis, the base member being movable through a plurality of positions and including a plurality of rods such that the suture may be sequentially disposed about the plurality of rods as the base member is moved through the plurality of positions; and
    a holder associated with the support member, the holder being configured to releasably engage the suture such that a predetermined amount of tension may be applied thereto.

2. The apparatus of claim 1, wherein the holder is repositionable between a first position and at least one subsequent position such that the suture may be oriented with respect to the longitudinal axis of the base member to define a desired angle therebetween.

3. The apparatus of claim 1, wherein the plurality of rods are configured in an arcuate arrangement.

4. The apparatus of claim 3, wherein the arcuate arrangement defines at least one array.

5. The apparatus of claim 1, wherein the base member is configured to receive a suture package.

6. The apparatus of claim 5, wherein the suture package is configured to releasably receive at least one needle, the suture extending from an end of the at least one needle.

7. The apparatus of claim 6, further including a needle holder disposed between the first array and at least one additional array.

8. The apparatus of claim 7 further including a mounting member disposed atop the base member, the needle holder being releasably engagable with mounting member.

9. The apparatus of claim 7, wherein the needle holder includes a plate having a plurality of buttons disposed thereon.

10. The apparatus of claim 9, wherein the buttons are arranged to define at least one channel, the at least one channel being adapted to releasably engage a needle, the suture extending from the needle.

11. The apparatus of claim 10, wherein the plate includes a post, a needle guide, and an end member, the post and the end member being spaced apart to define a suture channel therebetween that is configured to releasably receive the suture.

12. A method of winding a suture comprising the steps of:
    providing a winding apparatus including:
        a support member;
        a base member attached to the support member and defining a longitudinal axis, the base member being movable through a plurality of positions and including a plurality of rods such that the suture may be sequentially disposed about the plurality of rods as the base member is moved through the plurality of positions; and
        a needle holder associated with the base member, the needle holder being adapted to releasably receive a needle, the suture extending from the needle;
    positioning the needle within the needle holder;
    orienting the suture about the plurality of rods;
    positioning a first member of a retainer package about the needle and the suture;
    moving the base member through its plurality of positions such the suture defines a plurality of loops;
    positioning a second member of the retainer package atop the first member of the retainer package; and
    joining the first and second members of the retainer package.

13. The method of claim 12, wherein the step of providing a winding apparatus includes providing a winding apparatus including a holder associated with the support member and configured to releasably engage the suture.

14. The method of claim 13, further including the step of positioning the suture within the holder prior to moving the base member through its plurality of positions.

* * * * *